United States Patent [19]

Proudian, deceased et al.

[11] Patent Number: 4,917,097

[45] Date of Patent: Apr. 17, 1990

[54] APPARATUS AND METHOD FOR IMAGING SMALL CAVITIES

[75] Inventors: Andrew P. Proudian, deceased, late of Orangevale, Calif., by Sallee J. Proudian, legal representative; Michael J. Eberle, Citrus Heights; Adam D. Savakus, Loomis; Horst F. Kiepen, Georgetown; Douglas N. Stephens, Carmichael; David H. Rammler, Woodside; Claudia Zanelli, Sunnyvale, all of Calif.

[73] Assignee: Endosonics Corporation, Rancho Cordova, Calif.

[21] Appl. No.: 114,351

[22] Filed: Oct. 27, 1987

[51] Int. Cl.⁴ .............................................. A61B 8/12
[52] U.S. Cl. ............................ 128/662.06; 128/661.01
[58] Field of Search ............... 128/660, 661, 663, 772, 128/692, 344

[56] References Cited

U.S. PATENT DOCUMENTS

| | | | |
|---|---|---|---|
| 3,605,723 | 9/1971 | King et al. | 128/662 |
| 3,640,271 | 2/1972 | Horton | 128/662 |
| 3,827,115 | 8/1974 | Bom | 29/255.35 |
| 3,938,502 | 2/1976 | Bom | 128/662 |
| 4,127,034 | 11/1978 | Lederman et al. | 73/626 |
| 4,191,193 | 3/1980 | Seo | 128/675 |
| 4,211,949 | 7/1980 | Brisken et al. | 128/660 |
| 4,237,900 | 12/1980 | Schulman et al. | 128/630 |
| 4,274,423 | 6/1981 | Mizuno et al. | 128/675 |
| 4,325,257 | 4/1982 | Kino et al. | 73/626 |
| 4,386,339 | 5/1983 | Henry et al. | |
| 4,456,013 | 6/1984 | De Rossi et al. | 128/675 |
| 4,505,156 | 3/1985 | Questo | 73/626 |
| 4,576,177 | 5/1986 | Webster, Jr. | 128/660 |
| 4,589,419 | 5/1986 | Laughlin et al. | 128/663 |
| 4,641,657 | 2/1987 | Ellis | 128/660 |
| 4,665,925 | 5/1987 | Millav | 128/344 |
| 4,671,293 | 6/1987 | Shaulov | 128/660 |
| 4,771,782 | 9/1988 | Millar | |
| 4,771,788 | 9/1988 | Millar | |
| 4,794,931 | 1/1989 | Yock | 128/662.06 X |

FOREIGN PATENT DOCUMENTS 1402192 8/1975 United Kingdom .

OTHER PUBLICATIONS

"Signal Enhancement for Automatic Identification of Arterial Wall Echos from an Intravessel Scanner", R. W. Martin et al., Ultrasound in Medicine, vol. 4, (New York, 1978), pp. 417-431.

Black, William C., Jr., "High Speed CMOS A/D Conversion Techniques", University of California, Berkeley, Electronics Research Laboratory, Mem. No. UCB-/ERL M80/54, Nov. 1980, pp. 180-243.

Black, William C., Jr., "Time Interleaved Converter Arrays", IEEE Journal of Solid-State Circuits, vol. SC-15, No. 6, Dec. 1980, pp. 1022-1029.

Corcoran et al., "A 1 GHz 6b ADC System", Proceedings of IEEE International Solid-State Circuits Conference; IEEE 1987, pp. 102-103, 359-360.

Corcoran et al., "A 400 MHz 6b ADC", Proceedings of IEEE International Solid-State Circuits Conference; IEEE 1987, pp. 294-297, 357.

D. K. Peterson, G. S. Kino: "Real Time Digital Image Reconstruction: A Description of Imaging Hardware & An Analysis of Quantization Errors"; IEEE T-SU#31, pp. 337-351; 7/84.

A. B. Glaser, G. E. Subak-Sharpe: "Integrated Circuit Engineering: Section 6.6 Inverted Chips", Addison Wesley, MA, 1979.

(List continued on next page.)

Primary Examiner—Francis Jaworski
Attorney, Agent, or Firm—Leydig, Voit & Mayer

[57] ABSTRACT

An in vivo imaging device is provided for producing real-time images of small, moving or stationary cavities and surrounding tissue structure. The imaging device includes a probe assembly of very small dimensions and preferably sufficiently small to fit within cavities having a diameter on the order of that of a human coronary artery. The probe assembly may be mounted to a positioning device such as a catheter, which allows for the use of, for example, conventional guiding catheters and guide wires.

38 Claims, 10 Drawing Sheets

OTHER PUBLICATIONS

D. G. Weinstein: "Polyvinylidene Fluoride Acoustic Transducers and Imaging Arrays", Ph.D. Thesis, Stanford University, Oct. 1982.

R. G. Swartz, J. D. Plummer: "On the Generation of High-Frequency Acoustic Energy with Polyvinylidene Fluoride", IEEE T-SU #27, Nov. 1980.

Ohigashi et al., "Piezoelectric & Ferroelectric Properties of P(VDF-TrFE) Copolymers & Their Application to Ultrasonic Transducers", Ferroelectrics, vol. 60, pp. 263–276, 1984.

S. J. Norton, "Reconstruction of a Reflectivity Field from Line Integrals Over Circular Paths", J. Acous. Soc. Am., vol. 67, #3, pp. 853–863, Mar. 1980.

A. Macovski, "Ultrasonic Imaging Using Arrays", Proc. IEEE, vol. 67, #4, pp. 484–495, Apr. 1979.

Bennet, Peterson, Corl & Kino, "A Real-Time Synthetic Aperture Digital Acoustic Imaging System", Acoustical Imaging, vol. 10, pp. 669–692, Plenum Press, N.Y., 1982.

"Digital Reconstruction of Multidimensional Signals from Their Projections"; Mersereau and Oppenheim, IEEE, vol. 62, No. 10, Oct. 1974, pp. 1319–1338.

"An Ultrasonic Catheter for Intravascular Measurement of Blood Flow: Technical Details"; R. W. Martin and D. W. Watkins, IEEE, vol. SU-27, No. 6, 11/1980, pp. 277–286.

"A Digital Signal Processing Approach to Interpolation", R. W. Schafer and L. R. Rabiner, IEEE, vol. 61, No. 6, Jun. 1973, pp. 692–702.

"Analysis of a Scan Conversion Algorithm for a Real-Time Sector Scanner", M. H. Lee, J. H. Kim & S. B. Park; IEEE, vol. M1-5, No. 2, Jun. 1986, pp. 96–105.

APPARATUS AND METHOD FOR IMAGING SMALL CAVITIES

FIELD OF THE INVENTION

The present invention relates generally to the field of ultrasonic imaging, and more particularly to ultrasonic imaging to determine various characteristics of relatively small cavities and surrounding structures.

BACKGROUND OF THE INVENTION

In the United States and many other countries, heart disease is the leading cause of death and disability. One particular kind of heart disease is atherosclerosis, which involves the deposition of fatty material on the inside of vessel walls throughout the body (commonly called "plaque"). As the plaque collects, the artery narrows and blood flow is restricted. If the artery narrows too much, the heart muscle nourished by the artery receives insufficient oxygen and a myocardial infarction or "heart attack" can occur. Atherosclerosis can occur throughout the human body, however, it is most life threatening within the coronary vasculature.

Physicians have a wide range of tools at their disposal to treat patients with coronary artery disease. Coronary artery bypass grafts or "open heart" surgery can be performed to bypass blocked artery segments. Other, less invasive procedures are available. For example, some blockages may be dissolved by chemical treatment. Alternatively, a procedure known as percutaneous transluminal coronary angioplasty (hereinafter "PTCA") may be performed in which a catheter with an expandable section on its end is placed within the narrowed artery and inflated to compact the plaque against the vessel wall, thereby relieving the blockage.

No matter what method is used to treat coronary artery disease, it is necessary for physicians to obtain quantitative information on the condition of the vasculature within the heart. Traditionally, coronary angiography has been the method of choice. Coronary angiography involves the placement of the end of a catheter at the beginning of the coronary vasculature. A small amount of radiopaque dye is injected, and a X-ray motion picture is taken while the dye is pumped through the vessels. The physician then examines the pictures and looks for any telltale narrowing of the blood flow opacified by the radiopaque dye. By the number and degree of such narrowing, the course of treatment can be determined.

Angiography has the extreme limitation of indicating only where the blood is within the vessel; it reveals nothing of the condition of the inside of the vessel and the vessel wall itself. Furthermore, most angiography machines present virtually only one-dimensional projections of where blood flow exists. Because of this imaging limitation, the complex structures within the coronary vasculature often exhibit quite ambiguous images.

Recently, imaging of soft tissue such as gross cardiac structures has provided physicians with diagnostic images having quality that is unavailable from conventional techniques using X-ray radiation. In particular, magnetic resonance imaging (MRI) and ultrasound have become important diagnostic tools for cardiac assessment. Although MRI has the ability to image blood vessels, the image resolution is not sufficient to allow assessment of the condition of the walls of the vessel. Conventional ultrasound scanning also suffers from lack of resolution. More recently, high frequency (hence, high resolution) ultrasound has been used during open heart surgery to access the coronary arteries. This method requires the opening of the chest cavity to expose the heart surface and is hence limited in its application.

In an even more recent development, in vivo ultrasonic imaging of the human body creates the potential for access to a wealth of information regarding the condition of a patient's vasculature that is currently only at best indirectly available from other sources. The information received from in vivo imaging may be used as a diagnostic tool to help determine patient treatment, or as a surgical tool, supplementing angiography in PCTA.

In vivo ultrasonic imaging from within the heart has been described in U.S. Pat. No. 3,958,502 to Bom. In order to provide for ultrasonic imaging inside the human body, the Bom patent provides an array of small transducer elements which may be introduced into the body by way of catherization. The array of elements is excited at ultrasonic frequencies and the reflections or echos of the generated ultrasonic acoustic waves are detected by the piezoelectric properties of the transducers. Unfortunately, due to the nature of the material used for the transducers, the array of elements cannot be made small enough to allow passage into small areas such as the coronary arteries. Therefore, use of the Bom device is limited to within the heart chambers and the associated great arteries.

An additional limitation of the Bom device is the poor resolution caused by a sparse distribution of transducer elements. Piezoelectric materials of the type used by Bom (e.g., ceramics) have a practical limitation in size reduction. Because of this size limitation and the fact that the maximum resolution of the transducer array is limited by the center-to-center spacing of adjacent elements, the Bom device is inherently limited in the quality of its image resolution.

A further limitation of the Bom device is the fixed delays it provides for focusing an image. Such fixed delays do not provide satisfactory images for identification of tissue structures. For a satisfactory image, a dynamic focusing feature is needed to provide an optimal focus at a plurality of points in the imaging plane. One approach to implementing such a dynamic focusing feature is a so-called "synthetic focus" or "synthetic-aperture" approach disclosed in U.S. Pat. No. 4,325,257 to Kino et al.

For many diagnostic and therapeutic purposes, in vivo ultrasonic imaging must simulate real-time performance. To achieve diagnostic or therapeutic quality images in small cavities while maintaining real-time performance is a formidable task and one which applicants believe has not previously been attained.

SUMMARY OF THE INVENTION

It is a general object of the invention to provide diagnostic quality, virtual real-time ultrasonic images of small cavities and their associated surrounding structures from within the cavities.

It is a further object of the invention to provide a method of providing diagnostic quality, virtual real-time ultrasonic images that is sufficiently flexible to accommodate a range of ultrasonic imaging requirements from within small cavities.

It is a further object of the invention to provide an array of transducer elements for generating ultrasonic imaging data that is small enough to enter small cavities, yet also exhibit controlled behavior and is manufacturable on a commercial basis. In this connection, it is a related object of the present invention to maintain a high degree of sensitivity to signals from weak reflectors of ultrasonic signals, such as human vascular tissues, while maintaining the small size of the array of transducers.

It is another object of the invention to provide the physician with the ability to accurately position the array of transducers within the imaging area.

It is yet another object of the invention to minimize the number of wires required to connect the in vivo portion of the ultrasonic imaging device of the invention to an in vitro processing stage. In this connection, it is a related object of the invention to distribute the control of the excitation of the array of transducer elements between in vivo and in vitro sites.

It is still another object of the invention to electrically isolate the in vivo portion of the imaging device of the invention in order that it is safe for use in human imaging applications. In this connection, it is a related object of the invention to provide operation of the imaging device without causing significant risk to humans from excessive localized heating or radiation.

A still further object of the present invention is to operate at very low power dissipation in vivo in order to prevent heating of surrounding tissue and expansion of parts.

It is a further object of the present invention to provide an imaging device whose in vivo portion may be mounted to a positioning device such as a catheter, which allows the use of, for example, conventional guiding catheters and guidewires. In this connection, it is a related object of the present invention that the imaging device be suitable for incorporation into recent catheter systems, and allowing for the continued use of, for example, guiding catheters and guidewires, in conjunction with catheter-based diagnostic and therapeutic procedures such as angioplasty, regional therapy for dissolving plaque and the like.

Briefly, the invention provides an in vivo imaging device for producing realtime images of small, moving or stationary cavities and surrounding tissue structure that is uniquely and advantageously constructed using a conventional catheter assembly fitted at its end with a probe assembly for transmitting and receiving ultrasonic signals from elements of an array of ultrasonic transducers incorporated into the probe assembly. The transducer elements are selected and controlled by an in vitro electronic signal processing and imaging unit which transmits excitation and control signals via a transmission cable to integrated circuitry on-board the body of the probe assembly. The integrated circuitry routes excitation signals to the transducer elements in a predetermined sequence. The body of the probe assembly not only supports the array of transducer elements and the integrated circuitry, but also accommodates conventional catheter devices such as a catheter guidewire that may be threaded through the probe assembly.

The number of wires in the transmission cable connecting the integrated circuitry to the processing and imaging unit are minimized by providing for a multiplexing task at the integrated circuitry onboard the probe assembly. Due to the relatively few number of conductors comprising the transmission cable, there is a high degree of physical flexibility achieved, and there is a relatively small cross-section obtained, which makes the device convenient for use within the limited confines of its intended operating environment. The integrated circuits also buffer excitation signals from the transmission cable which are directed to a selected element in accordance with a preferred image reconstruction scheme. These pulses are converted into ultrasonic waves by the transducer elements. The echoes or reflections from the environment are received by the transducer elements, converted back into electrical signals which are relatively weak, and buffered by the integrated circuits so that the weak signals are boosted before being directed onto the transmission cable for delivery to the signal processing and imaging unit.

Because of the very small size of the probe assembly, the piezoelectric material used for the array of transducer elements is preferably continuous in order to simplify construction of the probe. Further, the material may be characterized by a high internal electrical impedance resulting in weak electrical output current in response to ultrasonic echos. In order to provide a wide beam pattern as desired by the preferred imaging technique, the transducer elements adjacent an element or elements receiving an excitation signal are shunted to a low impedance to confine the active region to the selected transducer or transducers.

Within the electronic signal processing and imaging unit, signals indicative of the reflections or echos of ultrasonic acoustic waves are processed at extremely high speeds such that signal digitization and dynamic digital signal averaging, with respect to each individual or group of transducer elements, may be implemented, thereby producing resultant signals having a very high dynamic range. These resultant signals are then processed into diagnostic information in the form of, for example, images. The signals are preferably processed using a synthetic-aperture approach wherein dynamic time delays and weighting factors are used to produce a myriad of individually focused points throughout the entire image plane, thereby resulting in real-time, high resolution diagnostic images of the cavity and surrounding structure.

BRIEF DESCRIPTION OF THE DRAWINGS

Other objects and advantages of the invention will be apparent from the following detailed description and the accompanying drawings, in which.

While the invention will be described in connection with angioplasty or PTCA surgery, it will be understood that it is not intended to be limited to such use. On the contrary, the invention is intended to cover all applications which may require imaging in a small cavity. An example of such an alternative application is the use of the invention on the end of a catheter without the incorporation of a balloon. A specific example of such a use is a pharmaceutically therapeutic use where cholesterol-inhibiting drugs are used for regional therapy and the imaging device of the invention is used to monitor the effectiveness of the drugs in removing plaque. Another specific example of an alternative use is a physical therapeutic use such as measuring blood flow rates (using Dopler sound imaging in conjunction with invention) or determining sizes and locations of gall stones and the like. Yet another example of an alternative application is the incorporation of the invention into a catheter in conjunction with a laser or like devices for burning plaque in the arteries.

DETAILED DESCRIPTION OF THE PREFERRED EMBODIMENT

Figure 1:
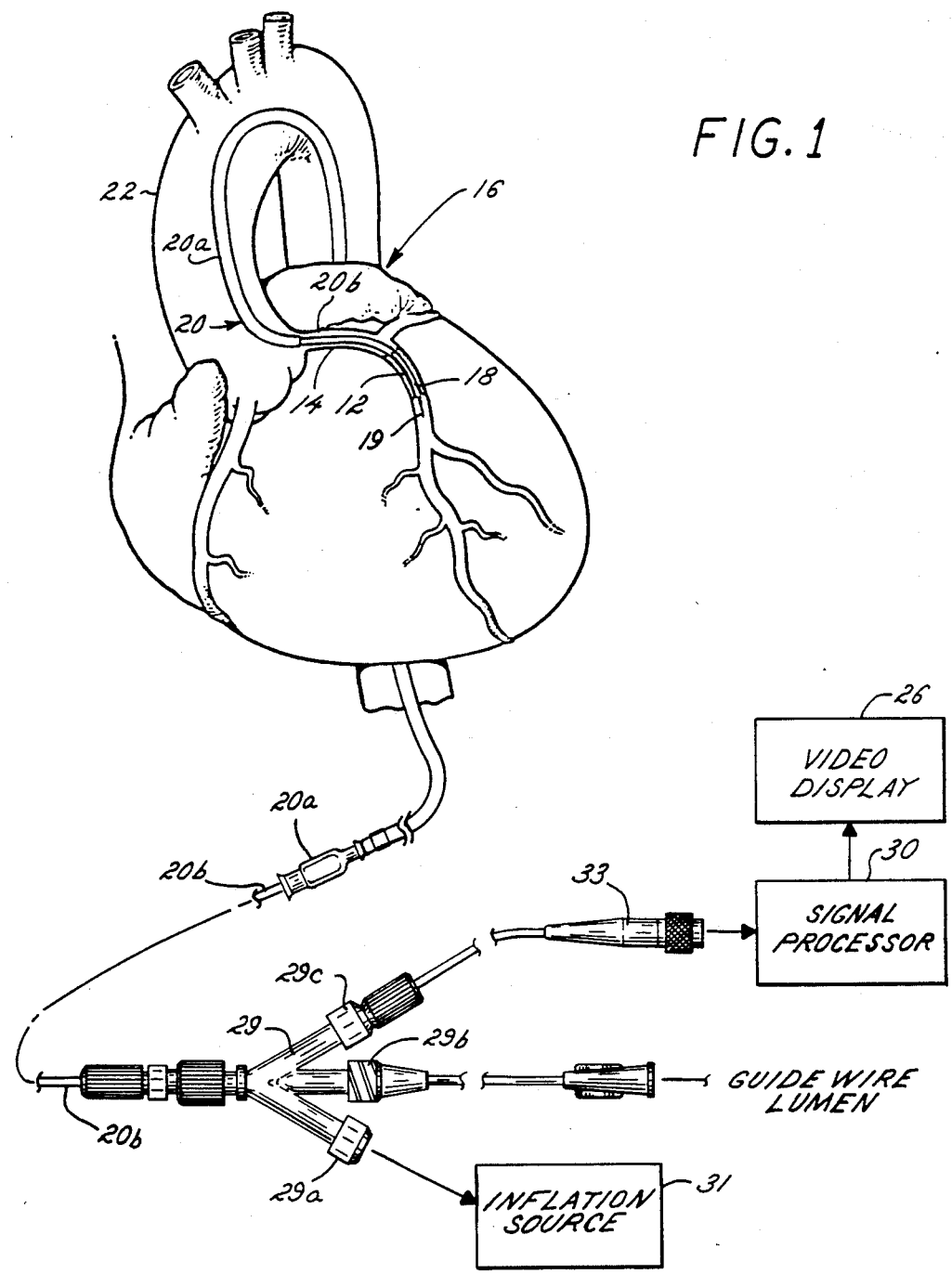
FIG. 1 is a system-type diagram of the ultrasonic imaging device of the invention, illustrating the use of the device to image a coronary artery during a PTCA procedure.

Turning to the illustrated embodiment and referring first to FIGS. 1-4, a buildup of fatty material or plaque 12 in a coronary artery 14 of a heart 16 may be treated in certain situations by inserting a balloon 18, in a deflated state, into the artery via a catheter assembly 20. As illustrated in FIG. 1, the catheter assembly 20 is a three-part assembly, having a guide wire 19, a guide catheter 20a for threading through the large arteries such as the aorta 22 and a smaller diameter catheter 20b that fits inside the guide catheter. After a surgeon directs the guide catheter 20 and the guide wire 19 through a large artery leading to the aorta 22, the smaller catheter 20b is inserted. At the beginning of the coronary artery 14 that is partially blocked by the fatty material 12, the guide wire is first extended into the artery, followed by catheter 20b, which includes the balloon 18 at its tip.

Once the balloon 18 has entered the coronary artery 14, an ultrasonic imaging device including a probe assembly 24 housed in the tip of the catheter 20b provides a surgeon with a cross-sectional view of the artery on a video display 26. Signals from the probe assembly 24, indicative of reflected ultrasonic waves, are transferred along a cable 28 to a signal processor 30 located outside the patient. The catheter 20b ends in a three-port junction 29 of conventional construction that couples the catheter to an inflation source 31, a guide wire source and the signal processor 30. The inflation and guide wire ports 29a and 29b, respectively, are of conventional PTCA catheter construction. The third port 29c provides a path for the cable 28 to connect with the signal processor 30 and video display 26 via an electronic connector 33.

As previously noted, the invention is not intended to be limited to a PTCA environment. In this regard, it will be appreciated that for use of the invention in a regional therapy application where cholesterol-inhibiting drugs are used, the port 29a may be an injection site for the drug instead of an inflation source and, of course, the balloon 18 at the end of the catheter 20b is not needed.

Figure 2:
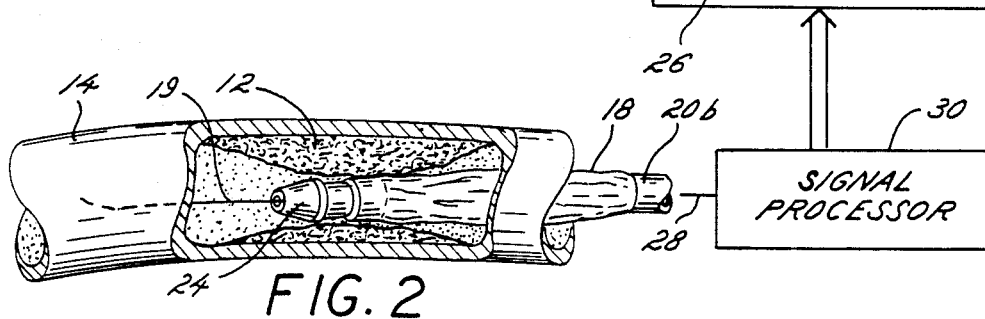
FIG. 2 is an enlarged and partially sectioned view of a portion of the coronary artery in FIG. 1, showing the probe assembly of the ultrasonic imaging device of the invention located at the tip of the catheter approaching an area of plaque buildup in the artery and the equivalent histologic view of the same to a surgeon.
Figure 3:
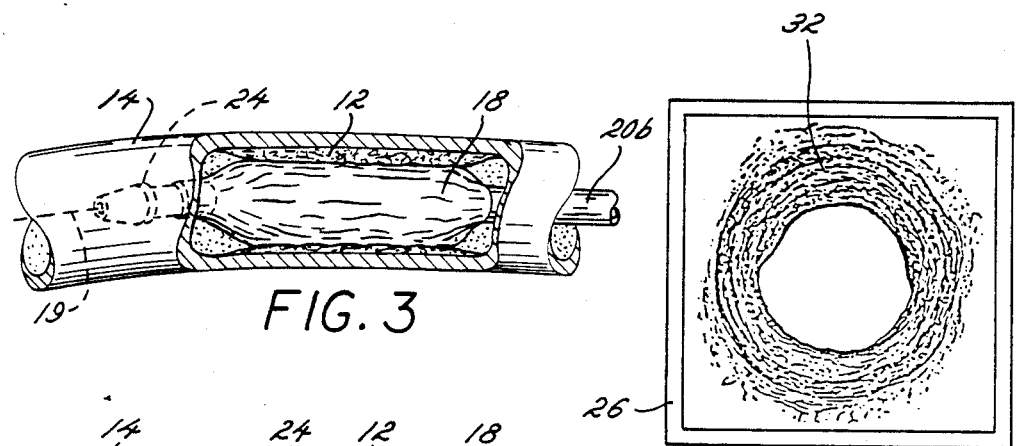
FIG. 3 is the same view as illustrated in FIG. 2, except the catheter has been further drawn into the area of plaque buildup in the coronary artery so as to bring a balloon section of the catheter into the area, where the balloon is inflated in order to compress the plaque in accordance with a standard PTCA procedure.
Figure 4:
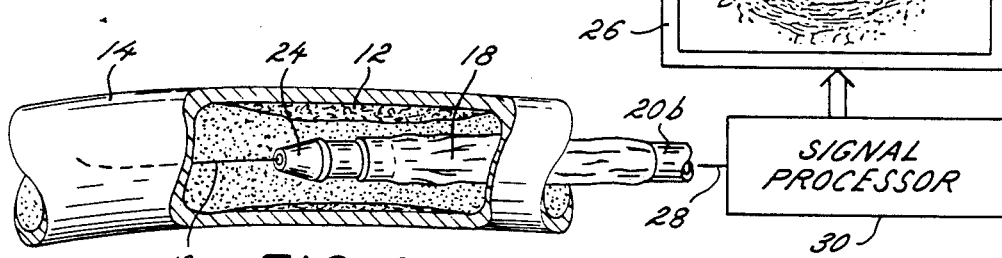
FIG. 4 is the same view as illustrated in FIGS. 2 and 3, except the catheter has been repositioned so that the probe assembly of the ultrasonic imaging device is in the area of the plaque buildup, and it is providing the surgeon with an image of the cross-sectional area of the coronary artery that can be used to determine how well the PTCA procedure opened the artery for additional blood flow.

Returning to a discussion of the invention in a PTCA application, the imaging device provides an image 32 on the display 26 that indicates when the balloon 18 is within a partially blocked area of the coronary artery 14 as is best seen in FIGS. 2-4. After locating the partially blocked area, the tip of the catheter 20a containing the probe assembly 24 is moved past the blocked area in order to bring the following balloon 18 into the area as shown in FIG. 3. The balloon 18 is thereafter inflated so as to compress the plaque 12 causing the blockage. Finally, the cardiologist may check the results of the PTCA procedure, by slightly withdrawing the catheter 20a in order to bring the tip and the associated probe assembly 24 back into the blocked area as shown in FIG. 4. If the PTCA procedure was successful, the image 32 on the video display screen 26 will show the lumen of the artery 14 has increased in cross-sectional area.

In practicing the invention, the probe assembly 24 is constructed to be sufficiently small to fit in cavities of approximately the size of a human coronary artery as shown in the illustrated embodiment. In order to provide for such small size, applicants have provided a unique and innovative construction for the probe assembly 24. First, a polymer piezoelectric material is used to provide transducer elements for generating and receiving ultrasonic acoustical waves. Preferably, the polymer piezoelectric material is continuous in order to provide for ease of manufacture. In the illustrated embodiment, the piezoelectric material forms a ring 44 for viewing in a plane P (FIG. 5) passing through the material and normal to its surface; however, it will be appreciated that in other applications or for viewing in alternative planes, the piezoelectric material may take other forms. To obtain good performance from the polymer piezoelectric material, it is necessary that the natural frequency of the material be much higher than the chosen operating frequency. In the illustrated embodiment, a frequency of 20MHz is chosen as the operating frequency.

Not all piezoelectric polymers are suitable for use as the ring 44. An acceptable material must have the following characteristics. The material must, of course, have good sensitivity characteristics for detecting reflected ultrasonic waves. Because of the small size and cylindrical shape of the ring 44, however, the piezoelectric material must also be capable of being formed into a suitable shape of very small diameter (e.g., a cylinder of about 1.5mm. diameter). For example, the material may start as a flexible sheet or, if it is not flexible, it may be formed directly into the desired shaped by deposition or other well-known forming processes. Also, because the material is continuous, it must be characterized by good acoustic behavior. In other words, excitation of one element in the array formed by the ring 44 must not generate shear waves or ringing from interaction with other elements in the array. As explained more fully hereinafter, the invention includes electronics that aid in eliminating shear waves or ringing. Furthermore, the piezoelectric material must be well matched to the human tissue immediately surrounding the probe assembly 24. For the foregoing criteria, applicants are presently employing the copolymer P(VDF-T,FE), having a thickness of approximately nine (9) microns. Other, alternative materials are PVDF, copolymer P(VDF-TFE), composites of polymers and ceramics (e.g., PZT), or a depositable material such as ZnO.

Because of the small size of the probe assembly 24, it will also be appreciated that a continuous ring 44 of material is much more preferable than an individual piece of piezoelectric material for each transducer element. The manufacturing complexities avoided and the cost savings obtained are considerable if a continuous ring of piezoelectric material is used. For example, using a continuous material, there is no need to cut individual elements. Cutting individual elements of the very small size required for the probe body 42 would be very difficult and expensive.

Of course, the piezoelectric polymer material comprising ring 44 must be supported, and the body 42 serves the purpose. Since acoustic energy is reflected at interfaces between regions of differing acoustic impedance, a hard backing for the transducer array is necessary to ensure that most of the ultrasonic energy is not absorbed by the backing. In the preferred embodiment, an alumina composition (i.e., $Al_2O_3$) of the body 42 provides the necessary hard backing.

Figures 5, 6, 7:
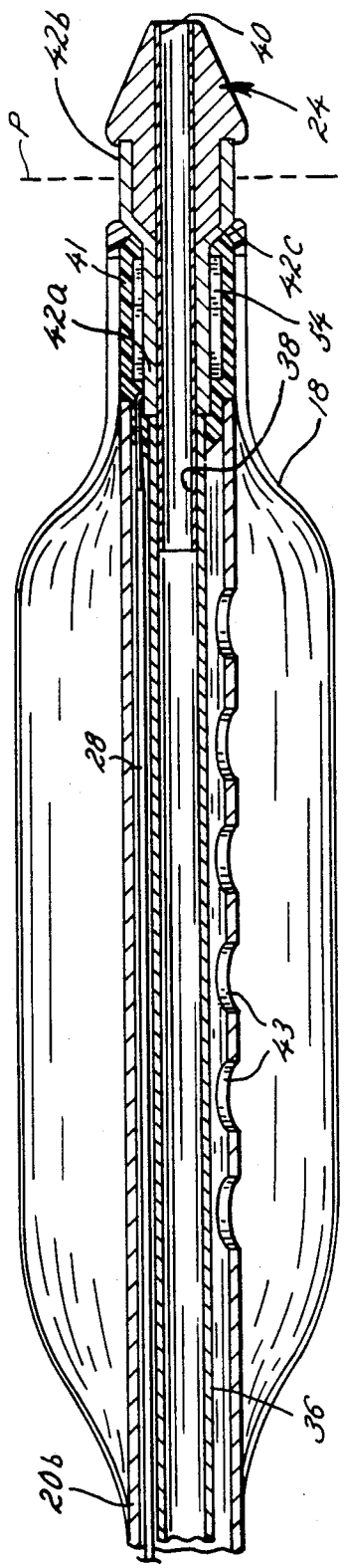
FIG. 5 is a cross-sectional view of the tip of the catheter in FIGS. 2-5, illustrating the probe assembly of the ultrasonic imaging device of the invention housed in the tip of the catheter and adjacent to its balloon section.
FIG. 6 is perspective view of the probe assembly of FIGS. 2-5 with the sheath and epoxy encapsulation covering the probe assembly removed to expose the underlying electronics and associated construction.
FIG. 7 is cross-sectional view of the probe assembly taken along the line 7—7 in FIG. 6.

As best seen in FIG. 6, the body 42 of the probe assembly 24 has box-shaped and cylindrically-shaped sections 42a, 42b, respectively. A third transitional section 42c joins the other two sections 42a, 42b by tapering the body 42 along its axial length from the cylindrical section to the box-shaped section. In order that the probe assembly 24 is sufficiently small to fit inside areas such as the coronary artery 14, it preferably has the following approximate dimensions: Diameter of cylindrical section 42b—1.5 millimeters; width of one side of box-shaped section 42a—3/4 millimeter; axial length—3.0 millimeters; diameter of axial bore 40 —½ millimeter.

The body 42 is formed by known injection molding techniques. Because the dimensions of the body 42 are small and the tolerances are small (e.g., the tolerance on the outer diameter of the cylindrically-shaped section 42b is 500 microinches), very precise machining is required for the injection mold. Furthermore, the small size of the body 42 makes it impractical to polish after molding. Therefore, it is important that the injection molding process provides a smooth surface.

It is an important feature of the invention that the body 42 of the probe assembly not interfere with conventional PTCA, regional drug therapy and other therapeutic or diagnostic procedures that utilize catheters and may advantageously incorporate the invention in order to improve those procedures. Therefore, in order to secure the probe assembly 24 to the tip of the catheter 20b, a conventional guide wire lumen inside the catheter is telescopically fitted over a mating guide wire lumen 38 forming the central bore 40 in the probe assembly as best seen in FIG. 5. To further secure the probe assembly 24, the end of the catheter 20b is joined to the probe assembly by way of an epoxy material 41 encapsulating and protecting the integrated circuits 54 mounted on the rectangular section of the body. By joining the probe assembly 24 to the catheter 20b in the foregoing manner, the ability of the catheter 20b to perform a conventional catheterization procedure is uneffected, since the bore 40 allows the guide wire to exit the tip of the probe assembly 24. To guard against possible contamination of blood caused by accidental contact of blood with the materials of the body 42, the bore 40 is lined with, for example, kapton. To further protect against contamination (and possible electrical shock), the outside of the probe assembly 24 is covered by a protective sheath (not shown) made of, for example, parylene.

As is well known in PTCA procedures, the catheter 20b supports the balloon 18 at its one end. In the preferred embodiment, the balloon 18 is positioned adjacent the probe assembly 24 and is isolated from ambient conditions by sealing the two ends of the balloon to the catheter in a conventional manner. The area of the catheter 20b covered by the balloon 18 includes a series of holes 43 for communicating fluid between the balloon and an inflation source 31 in FIG. 1.

Each wire in the cable 28 is formed of conventional "magnet" wire—i.e., a solid conductor protected by an insulating coating. Over the bundle of wires, a ribbon of copper (not shown) is spiraled in order to provide a ground shield for the signals carried by the cable 28. Preferably, the copper ribbon is provided with a protective insulating coating.

To provide an array of transducer elements for generating imaging data, a plurality of underlying conductive traces 46 are formed on the surface of the cylindrical section 42b of the body 42 and underlie the ring 44 of continuous piezoelectric material. In order to provide a ground plane for the transducer array, the outer surface of the ring 44 of piezoelectric material has a thin coating of metallic material. Each element of the array is defined by an area of the ring 44 overlapping the conductive traces as generally indicated in FIG. 7. In order to maintain the ring 44 of piezoelectric material at a fixed position over the conductive traces 46, a film of an epoxy glue holds the inner surface of the ring of material to the surface of the probe body 24. The ring 44 may be formed of the piezoelectric material as a cylinder or it may be a flat sheet that is rolled and joined at a seam. Preferably, the ring 44 is a seamless cylinder. The conductive traces 46 are evenly spaced about the circumference of section 42c of the body 42. Such a construction results in the elements of the array being aligned with their length axes parallel to the length axis of the body 42. Preferably, there are 64 conductive traces 46 and, therefore, 64 transducer elements.

To form the three-dimensional conductive pattern on the body 42 that includes the traces 46 defining the transducer elements and connections for the onboard integrated circuit chips 54, the body is first coated with a well-known titanium and tungsten mixture, using conventional deposition techniques. Over the titanium and tungsten mixture, a layer of gold is deposited onto the body 42. To etch the conductive pattern, the body 42 is held in a jig (not shown) and state-of-the-art laser oblation methods are used to etch the pattern on each side of the box-shaped section 42a, proceeding one side at a time. For the cylindrically-shaped and transitional sections 42b and 42c, respectively, each is etched separately by incrementally rotating the body in the jig.

In addition to not absorbing significant amounts of ultrasonic energy, the body 42 must not have resonant effects due to the energy reverberating in the cylindrically-shaped section 42b that are within the frequency region of operation. Such reverberation is evidenced by a notch in the frequency response of each element in the array. The frequency position of the notch is controlled by keeping the alumina under the transducer thin. In particular, the cylindrical section 42b of the probe body 42 is recessed so that the body defines a thin annular wall 48 for supporting the ring 44 of piezoelectric material.

Figure 9:
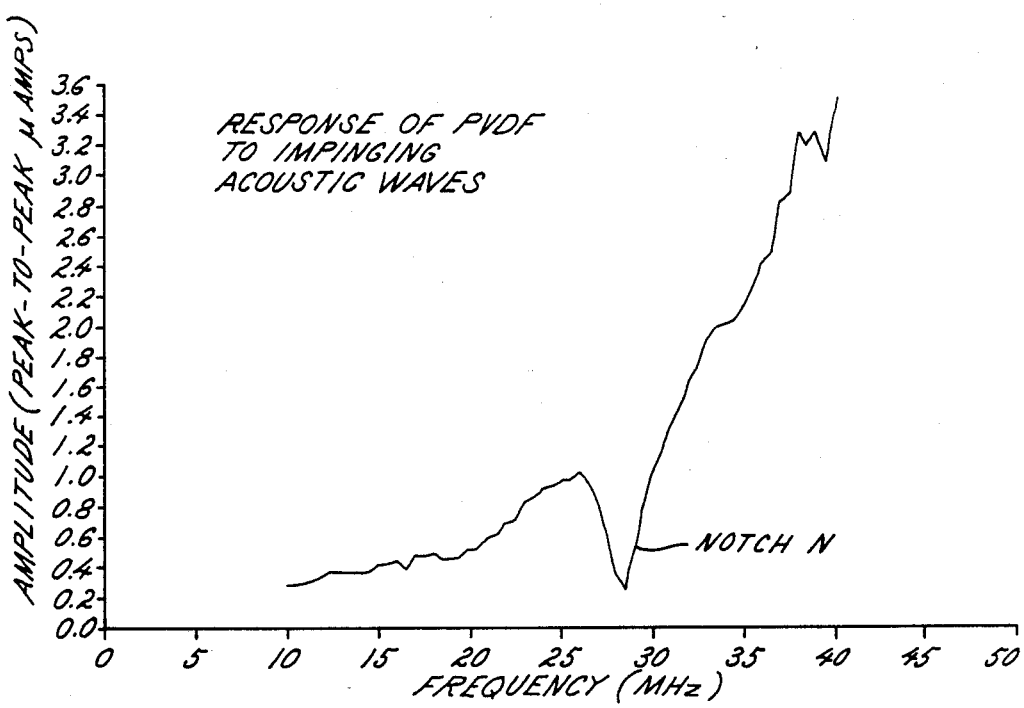
FIG. 9 is a graph illustrating an exemplary frequency spectrum echo response for one of the transducer elements defined by a conductive trace on the probe assembly and an overlying portion of a band of a piezoelectric polymer, where the abscissa is the frequency of the acoustic waves impinging on the transducer element measured in Megahertz and the ordinate is the electrical response of the piezoelectric polymer measured in microamps.

Referring to FIG. 9, the frequency response spectrum of the ring 44 of piezoelectric material includes a notch N whose frequency position in the spectrum is effected by the following factors: (1) the thickness of the wall 48, and (2) the acoustic velocity of the sound within the material comprising the wall. By controlling the thickness of the wall 48, the notch N is positioned outside the frequency region of the transducer array (e.g., 15–25MHz).

Figure 8:
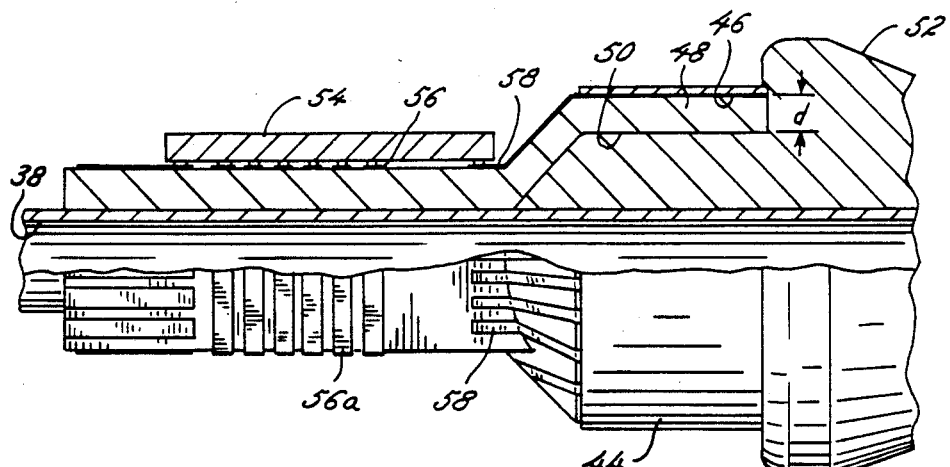
FIG. 8 is a side view of the probe assembly with a portion cut away to expose the composition of the body of the assembly along its longitudinal axis.

Quantitatively, the annular wall 48 has a thickness d as illustrated in FIG. 8 and destructive interference forming the notch N in FIG. 9 occurs when the half-wavelength λ/2 of the ultrasonic waves is approximately equal to the thickness d.

$$\lambda/2 \simeq d \tag{1}$$

More generally, destructive resonance occurs at all the odd half-wavelength harmonics.

$$n \frac{\lambda}{2} \simeq d \tag{2}$$

where n is an odd integer—i.e., 1, 3, 5, etc.

In order to ensure all the notches in the frequency response of the piezoelectric material occurs at a frequency above the bandpass frequency of the system, the first notch (N in FIG. 9) should be at no lower a frequency than, for example, 28MHz. Knowing the velocity V of the ultrasound waves through the alumina, equation (1) can be rewritten as $$\frac{V}{2f} \simeq d \tag{3}$$

where f is the frequency of the ultrasound waves. Substituting the values for equation (3) gives $$d = \frac{10.2 \text{ mm}/\mu \text{ sec.}}{2(28 \text{ cycles}/\mu \text{ sec.})} = .182 \text{ mm} \tag{4}$$

Therefore, the thickness of the annular wall 48 should be 0.182 mm or less. In order to fill the recess 50 formed by the annular wall 48 without significantly effecting the acoustic properties of the probe body, an acoustic backing material 52 such as urethane is used.

Figure 10:
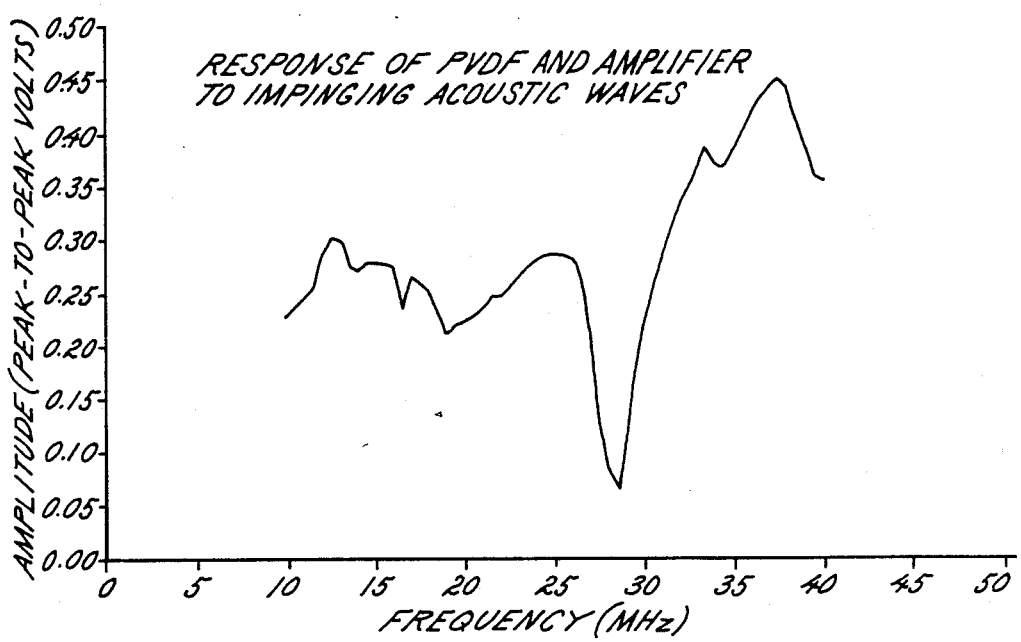
FIG. 10 is a graph similar to that of FIG. 9, except the frequency response of the transducer element is measured after it has been converted by a transimpedance amplifier configuration incorporated in integrated circuitry on-board the probe assembly, where the abscissa is still measured in megahertz but the ordinate is now measured in volts.

In accordance with one important aspect of the invention, because small piezoelectric transducers made from copolymers such as P(VDF-T,FE) are characterized by very high electrical impedance values (e.g., 30K ohms for one element), very low current signal levels are generated by each array element in response to reflected acoustic waves. In order to ensure these low current signals are not lost, and a high voltage signal is delivered to the signal processor 30, transimpedance amplifiers are located on-board the probe assembly 24 and in close physical proximity to the ring 44 of piezoelectric material. Preferably, the amplifiers provide current-to-voltage amplification in a linear relationship where one microamp produces approximately 750 microvolts. To provide these transimpedance amplifiers, the probe assembly 24 includes a plurality of the integrated circuit chips 54 (four in the preferred embodiment). Each chip 54 includes current amplifiers as discussed in greater detail in connection with FIG. 11 that receive low current signals from the high impedance transducer elements and provide the low impedance (e.g., 50 ohms) cable 28 with a high voltage signal. Although the actual amplifier devices for each channel are current amplifiers with an approximate gain of 15 from transducer element to cable, the overall effect of the amplifiers is one of transimpedance since the signal is received from a high impedance current source (the element) and delivered to a low impedance load as a voltage (the cable and its termination). FIG. 10 illustrates the frequency response of an element in the transducer array with the transimpedance amplifier and additional voltage amplification.

In order to physically fit the integrated circuit chips 54 onto the body 42 of the probe assembly 24, the four integrated circuit chips 54 are of an inverted chip design and are bonded to conductive pads 56 formed on the box-shaped section 42a of the probe body. The pads 56 interconnect each of the four chips 54 and also provide a connection between the chips and the cable 28 within the catheter 20a that connects the chips to the signal processor 30 outside of the patient. In order to provide communication between the conductive strips 46 which form the transducer elements and the chips 54, the strips extend along the axial length of the probe 24, beyond the ring 44 of piezoelectric material and down the transitional section 42c to conductors 58 on the underside of the chips 54.

In accordance with another important aspect of the invention, the cable 28 from the signal processor 30 provides communication channels between the processor and the integrated circuits 54, using a minimum number of wires. The four integrated circuit chips 54 provide a multiplexing function that distributes excitation pulses from the signal processor 30 to a predetermined one or ones of the transducer elements. In the preferred embodiment, a single pair of wires T+, T− in the cable carry the excitation signals as differential pulses in series format from the signal processor 30 to the chips 54. At the chips 54, each excitation signal is routed to an appropriate one of the transducer elements in order to execute an excitation sequence used by the preferred image reconstruction technique. By minimizing the number of wires required to carry the excitation signals to each of the transducer elements (e.g., 64 in number), not only is the problem of fitting a bulky cable in catheter 20b overcome, but also overcome is the problem of providing more than 64 contacts on the surface of the very small body 42.

Figure 11:
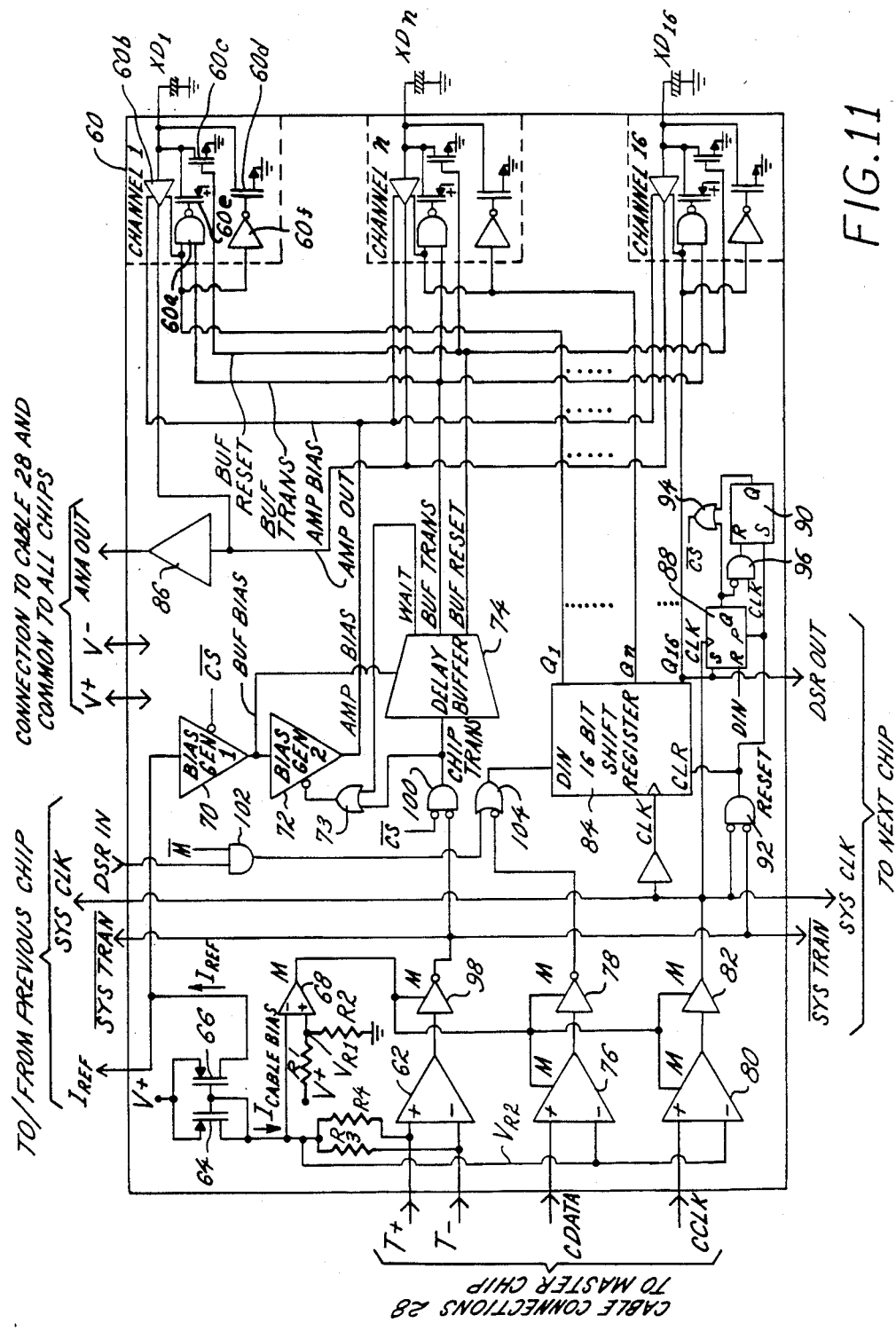
FIG. 11 is a schematic block diagram of the electronic circuitry contained in each of the plurality of chips mounted to a carrier portion of the probe assembly.

Each chip 54 as illustrated in FIG. 11 has 16 channels 60 associated with 16 of the 64 transducer elements $XD_1-XD_{64}$ defined by the ring 44 of piezoelectric material and the conductive traces 46. Each chip 54 is responsible for sequentially transmitting and receiving ultrasonic signals on one of its associated 16 channels. At any given time, exactly one of the chips 54 will be designated as active, where "active" indicates the one chip 54 that is currently exciting one of its associated transducer elements $XD_N$. Furthermore, at any given time only one of the 16 channels 60 on an active chip 54 is free to be excited by an excitation signal or to receive reflections or echos. The electrical signals generated from the reflections impinging on the free transducer element are amplified and sent via the transmission cable line 28, to the externally located signal processor 30 as explained more fully hereinafter.

Each excitation signal intended for one of the transducer elements $XD_N$ travels down the transmission lines T+, T− as a differential pulse. Preferably, the excitation signal consists of two closely spaced short duration (of approximately 25 nanoseconds) pulses. An excitation signal of this form generally provides significantly more transmitted acoustic energy from an excited transducer than would a single pulse. By empirical methods, an optimization is realized between maximizing the transmitted acoustic amplitude and maintaining reasonable image resolution. Furthermore, since the control of this pulsed excitation signal is accomplished externally at the signal processor 30 through the T+ and T− transmission cable lines 28, the particular form of this signal can be modified to maximize the desired features of the signal.

At the master chip 54, this differential pulse is received and amplified by the differential pulse receiver amplifier 62 as shown in FIG. 11. By transmitting the excitation signal as a differential pulse, the signal is substantially immune from the problems of electromagnetic interference. Preferably, the differential pulse is supplied to the T+ and T− transmission cable lines 28 via an analog buffer (not shown) which converts a received unipolar excitation signal from the signal processor 30 into the desired differential pulse.

To distribute the excitation signals to the correct one of the 64 channels, only one of the chips 54 receives timing signals on lines CDATA and CCLK and an excitation signal on line T+,T− from the transmission cable 28, although all four of the chips are capable of receiving these signals because of their identical structure. This one chip 54 receiving timing and excitation signals cooperates with the other three chips in a master-slave relationship where the signal lines CDATA, CCLK and T+,T− are used to generate a system clock (i.e., SYS CLK) for synchronizing all four chips 54, and to distribute the excitation signal T+,T− by way of line $\overline{\text{SYSTRAN}}$.

In order to provide communication between all of the chips 54, bus lines are common to all the chips and are connected between adjacent chips by extensions 56a of conductive pads 56, which are formed around the box-shaped section 42a of the body 42 (FIGS. 6 and 8). The bus comprises lines $I_{REF}$, $\overline{\text{SYSTRAN}}$, ANA OUT, SYS CLK, V+ and V−. In order to best describe the operation of the four chips 54, the schematic diagram of one of the chips in FIG. 11 will be treated as the master chip which receives the signal lines CDATA, CCLK, T+,T− and V+, V− from the transmission cable 28.

The $\overline{\text{SYSTRAN}}$ line delivers the excitation signals to all the chips 54, and as will be described in more detail later, other signals are used to control the application of the excitation signals to the 64 transducer elements $XD_1-XD_{64}$. (FIG. 11 shows 16 elements on one of four chips for a total of 64). In order to generate an excitation signal on the $\overline{\text{SYSTRAN}}$ line, a receiver amplifier 62 on the chip 54 receives the excitation signal in its differential pulse form and converts it to a unipolar form. From the receiver amplifier 62, the excitation signal is passed through an inverting buffer 64 which supplies an inverted version of the excitation signal to all the chips through the common $\overline{\text{SYSTRAN}}$ line.

In order to generate the signal on the common line $I_{REF}$, the master chip 54 responds to external bias currents on lines T+, T− by generating a cable bias current $I_{CABLE\ BIAS}$ which is used as a bias reference signal for indicating which chip 54 is the master chip receiving the timing and excitation signals. From the cable bias current $I_{CABLE\ BIAS}$, the reference current $I_{REF}$ is generated and distributed to all the chips 54 for producing the necessary bias voltages on the other chips. Specifically, the current $I_{REF}$ is generated at the drain of MOSFET 66 in the transistor current mirror 64, 66 on the master chip 54. The reference current $I_{REF}$ is used by bias generators 70, 72 to produce bias voltages for a delay buffer 74 and the individual channel amplifiers 60b which are discussed more fully hereinafter.

The cable bias current $I_{CABLE\ BIAS}$ is generated by a current mirror transistor configuration comprising two p-channel MOSFET transistors 64, 66 with their gates connected in common, and their sources connected to a positive supply voltage V+, as shown in FIG. 11. The gate of one MOSFET transistor is also connected to its drain which in turn is connected to the T+ and T− lines of cable 28. The voltage of the T+ and T− transmission cable lines of the master chip 54 are held at a voltage lower than the positive supply voltage V+, and as a result of this lower voltage, the cable bias current $I_{CABLE\ BIAS}$ flows from the common gate and drain connection of the transistor 64 located on the master chip 54.

In order to distinguish the master chip 54 from the other chips, the cable bias current $I_{CABLE\ BIAS}$ is utilized to assert a "M" line on the master chip 54. By contrast, the other chips 54 will have no cable bias current flowing, due to the absence of the T+ and T− transmission cable connections, and will have a negated "M" line. Specifically, for each chip 54 to determine if it is the master chip and either negate or assert its "M" line, a comparator 68 is used to compare the voltage level of the cable bias current on the line $I_{CABLE\ BIAS}$ to a predetermined comparator reference voltage $V_{R1}$ derived from series resistors $R_1$ and $R_2$. For the chips 54 not connected to the T+ and T− transmission cable lines, the line for a cable bias current $I_{CABLE\ BIAS}$ remains at the supply voltage V+ which is greater than the reference voltage $V_{R1}$, thereby causing the comparator 68 to negate the "M" line which designates the chip as a slave chip. Otherwise, if the T+ and T− transmission lines of the cable 28 are connected, there will be a voltage drop on the $I_{CABLE\ BIAS}$ line. This reduced voltage level will be lower in magnitude than the comparator reference voltage $V_{R1}$, thereby causing the comparator 68 to activate the "M" line which designates the chip as the master chip.

From the foregoing description, it will be appreciated that only one of the four chips 54 is designated as the master chip and accordingly only the master chip has an asserted "M" line, due to the presence of the T+ and T− connections from cable 28. The other three chips 54 have negated "M" line, due to the absence of a connection to the T+ and T− lines and are therefore slave chips in the sense that they are controlled by way of the master chip. As discussed more fully hereinafter, the state of the "M" line is used in other areas of the chip circuitry to determine whether or not a particular chip 54 is the master chip.

Timing signals received by the CDATA and CCLK lines are also dependent upon reference voltages generated by the current $I_{REF}$ or $I_{CURRENT\ BIAS}$. For example, on the master chip 54, the signal on the CDATA line is input to an amplifier 76 along with a reference voltage $V_{R2}$ generated at the node connecting resistors $R_3$ and $R_4$ from the $I_{CABLE\ BIAS}$ circuitry. This input amplifier 76 insures the proper voltage levels on the chip 54. The output of this input amplifier 76 is sent to an inverting buffer 78 that acts as a transmission gate which is controlled by the state of the "M" line. As for the CCLK transmission line from cable 28, it is connected through an input amplifier 80 along with the aforementioned reference voltage $V_{R2}$. The output of amplifier 80 is sent to a non-inverting transmission gate buffer 82, which in turn produces the clock signal SYS CLK on the common bus line for distribution to all the chips 54. This clock signal SYS CLK is used to sequence the shift register 84 on each chip 54 in order to sequentially activate the 64 channels 60 on the probe assembly 24 as explained more fully hereinafter.

Turning to a detailed discussion of the excitation of the 64 transducer elements, the sequential stepping through the 16 channels 60 on each of the chips 54 is accomplished by shifting a single logic bit through the 16 bit shift register 84. The logic outputs of the shift register 84 of an inactive chip 54 are all negated. Therefore, at any given time exactly one of the 16 outputs of the shift register 84 on one of the chips 54 is "active" and all the other 63 outputs are disabled. The CLK input to the shift register 84, driven by the SYS CLK bus line, allows the logic bit to be sequenced from one output $Q_N$ to the next $Q_{N+1}$. Each of the output lines $Q_N$ of the shift register 84 is used to sequentially and individually enable the transducer channels 60 on the chip 54 by way of a NAND gate 60a and an enable input to the corresponding channel amplifier 60b. As indicated in FIG. 11, there is a one-to-one correspondence between the individual outputs $Q_N$ of the shift register 84 and the individual transducer channels 60. For example, output $Q_1$ is associated with channel 1, output $Q_2$ is associated with channel 2, etc.

A separate chip select signal $\overline{CS}$ is asserted by the one of the four chips 54 that is currently activating one of its channels 60 for the generation and detection of ultrasonic acoustic signals. At this time, chip select lines $\overline{CS}$ of the other three chips 54 are negated. The $\overline{CS}$ signal is asserted by using one clocked SR flip-flop 88 and one unclocked SR flip-flop 90 as explained more fully hereinafter.

Two bias generator amplifiers 70, 72 on each chip 54 are responsible for producing the desired bias voltages needed for the operation of each chip. The first bias generator 70 receives as an input the common reference current $I_{REF}$ which is generated on the master chip 54, and utilizes this signal to produce the desired bias voltage on a BUF BIAS line for the delay buffer 74. Since the presence of a bias voltage on the BUF BIAS line is only needed for a particular chip 54 when one of its channels 60 is active, the $\overline{CS}$ (inverted chip select) line is used to selectively activate and de-activate the bias generator 70. The second bias generator 72 is used to provide the proper bias voltage on a AMP BIAS line for the transducer channel amplifiers 60b. The second bias generator 72 is selectively activated and de-activated by the logical ORing of the CHIP TRANS line (an inverted $\overline{SYSTRAN}$ line) and a WAIT line from the delay buffer 74 at OR gate 73. In order that a channel amplifier 60b transmits only signals from reflected acoustic waves impinging on the associated transducer element, the amplifier is activated only after a channel 60 has generated ultrasonic acoustic waves. To activate a channel amplifier 60b, the bias voltage AMP BIAS line is supplied to the amplifiers by the second bias generator 72 after the associated transducer element $XD_N$ has been excited to generate ultrasonic acoustic waves.

Figure 12:
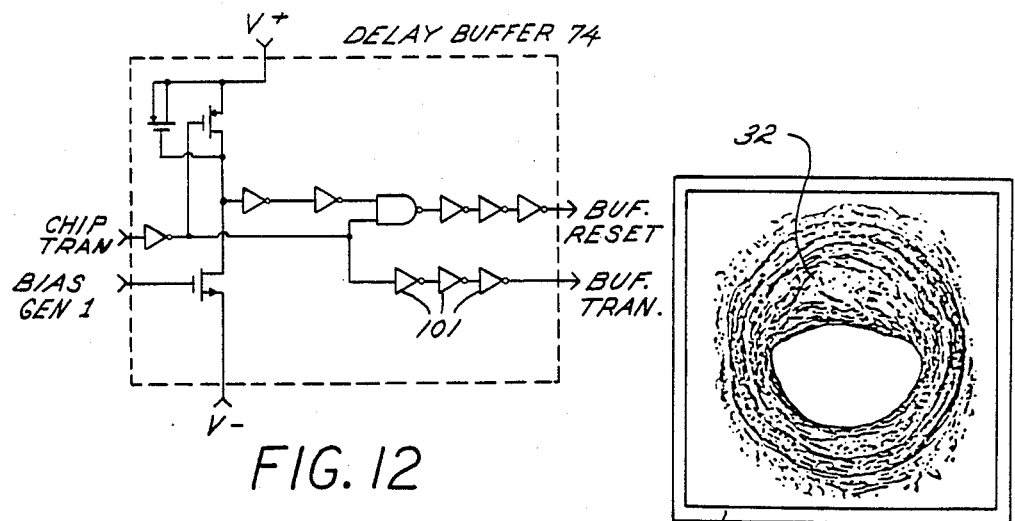
FIG. 12 is a detailed component diagram of a delay buffer which provides important timing signals in the electronic circuitry of FIG. 11.

As the foregoing discussion suggests, the delay buffer 74 serves an important timing role in the operation of the chips 54. A particular embodiment of the delay buffer 74 is illustrated in FIG. 12. It will be appreciated, however, that many alternative designs may also provide the desired timing signals of WAIT and BUF RESET.

Using the excitation signal on the CHIP TRANS line as its input along with the bias voltage BUF BIAS from the first bias generator 70, the delay buffer 74 produces three important output signals. Specifically, upon receiving an excitation signal on the CHIP TRANS line (via the lines T+ and T− of the transmission cable 28), the delay buffer 74 sets the WAIT output line active, thereby disabling the second bias generator 72 from producing a bias voltage AMP BIAS for the channel amplifiers 60b of the channels 60. After sufficient time has passed to ensure the WAIT line is high and the channel amplifiers 60b are deactivated (a delay is provided by the inverters 101 in FIG. 12), the delay buffer 74 sends the excitation signal on the BUF TRANS bus line, thereby sending the excitation signal to all of the transducer channels 60. In each channel, the BUF TRANS line is NANDed with one of the $Q_N$ outputs of shift register 84 by the NAND gate 60a and buffer FET 60e. Because only one NAND gate 60a in the channels 60 of chip 54 has both inputs active, only one of the transducer element $XD_1$-$XD_{16}$ is excited.

In accordance with another important aspect of the invention, the beam pattern formed by the excitation of an element is optimized during both transmission and reception of ultrasonic waves by providing low impedance paths through elements adjacent the excited element. The low impedance characteristic of adjacent elements minimizes the aperture width, thereby creating a beam of maximum width. Using the synthetic-aperture approach for creating an image on the video display 26, the widest beam is most desirable since it provides the greatest overlap with adjacent beams and hence the most information during reconstruction of an image. In order to provide the low impedance characteristic for adjacent elements, each channel 60 includes a MOSFET 60d controlled at its gate by a $\overline{Q_n}$ signal (i.e., $Q_n$ from shift register 84 inverted by inverter 60f). With the drain of the FETs 60d connected to the active node of a transducer element $XD_N$ and the source connected to the ground, an active Qn signal causes the node of the transducer element (i.e., the conductive trace 46) to be effectively grounded, thereby shunting the high impedance transducer element. At any given channel 60, the node for the transducer element remains grounded and the element shunted until the associated Qn line from the shift register 84 becomes active. With Qn active, the FET 60d is turned off and the transducer node is released from a ground potential so that it may deliver an excitation signal to the transducer element $XD_N$.

In keeping with the invention, after the excitation signal is received by the selected one of the transducer elements $XD_N$ on the BUF TRANS line, the BUF RESET line is briefly asserted by the delay buffer 74 in order to clamp the MOSFET transistors 60c to ground such that the excited transducer element is effectively shunted in order to sweep off any charge at the node of the excited element (to rapidly return the amplifier 60b to its quiescent bias state) and quell any transient signals or "ringing" at the input to the amplifier 60b. After any excessive charge at the node of the excited element and any ringing can be safely assumed to have dissipated, the signal on the BUF RESET line resumes its normally negated state until the next transmission cycle, thereby freeing the just excited transducer element to respond to reflected ultrasonic acoustic waves.

After the brief shunting of the transducer elements $XD_N$ by the clamping of the FETs 60c, the delay buffer 74 negates the WAIT line which in turn asserts the AMP BIAS line from the second bias generator 72, thereby turning on the channel amplifiers 60b. With the AMP BIAS line active, the one of the channel amplifiers 60b (as determined by the $Q_N$ outputs of shift register 84) amplifies the current signal received from the associated transducer element $XD_N$ and delivers a current signal at the AMPOUT line.

Upon the starting of operation of the device, an asynchronous RESET signal is generated by strobing the T+,T− and CCLK lines so as to bring the $\overline{SYSTRAN}$ and SYS CLK bus lines both to logic states necessary to produce an asserted RESET signal by logic gate 92. This asserted RESET signal is input to the S input of the unclocked SR flip-flop 88. It also clears the 16-bit shift register 84 and presets the clocked SR flip-flop 90. In response to this RESET signal, the unclocked SR flip-flop 90 output is asserted as well as the clocked SR flip-flop output 88. Due to the ORing of the outputs of the clocked and unclocked SR flip-flops 88 and 90, respectively, a negated $\overline{CS}$ chip select signal is produced from an OR gate 94. Note that all chips are inactive during the reset. After the chips 54 have been reset and normal chip operation is desired, both the $\overline{SYSTRAN}$ and the SYS CLK lines are brought back to their quiescent active state.

In order to begin transmitting and receiving after resetting the chips 54, the first transducer channel 60 on the master chip is activated. This is accomplished by loading a data bit into the shift register 84 on the master chip 54 by asserting the CDATA line followed by one clock pulse. The "DSR IN" line from the $Q_{16}$ of the shift register 88 on the previous chip 54 is asserted (if the presently active chip is a slave) and ANDed with the "$\overline{M}$" line (inverted "M" signal) at AND gate 102 to produce a signal which is ORed with the CDATA signal at OR gate 104. The resulting signal is shifted into the DIN input of the shift register 84 of the master chip in response to clock pulse on the SYS CLK line.

After a data bit has been loaded into the 16-bit shift register 84, the process of transmitting and receiving sequentially through all the transducer channels 60 on the device begins. As the data bit from CDATA is shifted through the $Q_N$ outputs of the shift registers 84 of the four chips 54, it sequentially activates the 64 channels 60 and their associated transducer elements $XD_1$-$XD_{64}$ of which "Qn" denotes which transducer channel 60 is active.

For example, channel 1 of the master chip 54 is made active in response to the presence of the data bit on the $Q_1$ line of the 16-bit shift register 84. An excitation signal in a differential pulse format is then sent to the master chip 54 via the T+ and T− transmission lines of cable 28. As previously discussed, this signal is then converted to the $\overline{SYSTRAN}$ signal by way of amplifier 62 and inverting buffer 98. For delivery to the delay buffer 74, the $\overline{SYSTRAN}$ signal is inverted at the input to AND gate 100. The other input to the AND gate 100 is an inverted chip select signal $\overline{CS}$. Since the $\overline{CS}$ signal for the master chip 54 is currently asserted, the excitation signal passes through the AND gate 100 and into the delay buffer 74. As previously explained, the delay buffer 74 sends the excitation signal on the BUF TRANS line to the transducer channels 60.

In keeping with the invention, the transimpedance amplifiers included in each chip 54 are implemented by series connected current amplifiers 60b and 86. Each of the amplifiers 60b and the amplifier 86 has a nominal gain of approximately five for the amplifiers 60b and three for the amplifiers 86. Ultrasonic acoustic signals generated by a transducer element $XD_N$ are reflected as they propagate through the coronary artery and into the surrounding tissue. These reflected acoustic waves impinge on the transducer element $XD_N$, and are converted to electrical signals amplified by the channel amplifier 60b before being sent to the AMP OUT bus line as previously explained. From the AMP OUT bus line, the signals indicative of the reflected ultrasonic waves are delivered to the amplifier 86, thereby multiplying the AMP OUT bus current to a level acceptable for transmitting on the analog output line ANA OUT of the transmission cable 28 for transmitting the signals to the external signal processing stage 30. The signals on the ANA OUT line represent the relative amplitudes of the reflected ultrasonic waves and accordingly contain important timing information about the path length of the reflected ultrasonic waves and the density of the reflecting medium.

After the transmitting and receiving process has been completed on all the 16 transducer elements 60 of the master chip 54, the master chip is deactivated and the next of the three slave chips is activated. This is accomplished through the connection of the $Q_{16}$ output of the shift register 84 to DSR OUT which is connected to the DSR IN input line of the next chip by means of the traces 56a around the body 42. The data bit at $Q_{16}$ is shifted into $Q_1$ of the shift register 84 in the neighboring chip 54 upon the cycling of the CCLK line. The input line to the next chip (DSR IN) is ANDed with the " " line at AND gate 102 which is then ORed with the CDATA line at OR gate 104 and input to the 16-bit shift register 84. Since this next chip 54 is not the master chip (the description started with the master chip), the " " line will be asserted which allows the passage of the data bit on the DSR IN line from the $Q_{16}$ line of the previous chip to the input DIN line of the data shift register 84 of the next chip. At the occurrence of the clock pulse of the SYS CLK line, the master chip 54 is deactivated (i.e., its chip select $\overline{CS}$ is negated) and the next chip is activated (i.e., its chip select $\overline{CS}$ is asserted).

More specifically, the previous chip is deactivated due to the connection of the $Q_{16}$ output of the shift register 84 to the S input of the clocked flip-flop 88, thereby negating the $\overline{CS}$ signal. The next chip 54 is activated as a result of the SYS CLK cycling and resetting both RS flip-flops 88, 90 which asserts the chip select line $\overline{CS}$. Since the signal at the DIN line (which is in effect the $Q_{16}$ output from the previous chip) is also connected to the R input of the clocked flip-flop 88, an asserted $\overline{CS}$ signal results which designates this next chip 54 as active.

Now that the next chip 54 is activated, the transmitting and receiving process is done in sequence for each of the 16 transducer channels 60 on this chip in the same manner previously described for the master chip. After this process is completed, this chip 54 will be deactivated and the next chip (second slave) will be activated in the same manner as previously described. The same process continues until all 64 transducer elements $XD_N$ have been excited. After all the transducer elements $XD_N$ of the last chip 54 have been sequenced through for transmitting and receiving, another data bit is sent via the transmission cable 28 to the CDATA line of the master chip 54 to begin the entire process again, starting from the first transducer channel 60 on the master chip.

In summary, the chips 54 located on the probe assembly use the excitation and control signals supplied via the transmission cable 28 to sequentially generate and detect ultrasonic acoustic waves from individual transducer elements $XD_N$. The detected reflections of ultrasonic waves are first converted to electrical signals, amplified and then sent via a transmission line in cable 28 to the external signal processing stage 30. The signals sent to the external signal processing stage 30 contain important amplitude and timing information which is essential to reconstruct images of the cavity in which the probe assembly 24 is operated. During operation of the probe assembly 24, only one of the several chips 54 is active at any given time, and only one of the transducer elements $XD_N$ associated with the active chip is transmitting and receiving. After all the transducer elements $XD_N$ of a particular active chip 54 have been sequenced through, the chip is deactivated and the next chip is activated. This sequencing of the transducer elements $XD_N$ continues on each of the next chips 54, and then is repeated continuously in order to provide real-time signals for the external signal processing stage 30 to produce images.

It should be noted that although applicants preferred to transmit and receive on the same single channel, other alternatives are also possible. For example, a first channel 60 may transmit ultrasonic waves in response to the excitation signal and a second channel may be made available to receive the reflected ultrasonic waves. Also, it may prove desirable to transmit or receive on more than one channel 60. Because these alternatives involve changes to the illustrated embodiment of chip 54 that will be readily discernable to those skilled in the art, such changes are not discussed in detail herein.

Turning now to a consideration of the external signal processing system 30 used to reconstruct images from the signals received from the probe assembly 24 of FIGS. 1-12, ultrasonic signals are received by the processing system from the probe assembly via the line ANA OUT of the transmission cable 28. Preferably, the received signals are amplified at a receiving amplifier and then passed to an analog-to-digital (A/D) converter.

In accordance with yet another important aspect of the invention, each transducer channel 60 is controlled by the signal controller 30 to transmit and receive ultrasonic signals a plurality of times (e.g., 100 times) before the active shift register 84 sequences the associated chip 54 to the next channel. Because the probe assembly 24 is intended for imaging in very small areas such as a coronary artery, the two-way path of a generated and reflected signal is short (e.g., eight millimeters) and as a result of this short path the time delay for receiving a reflected signal is also very short (e.g., five to ten microseconds). Because of the short amount of time consumed for detection of a reflected signal, each transducer element $XD_N$ may be excited multiple times, and the reflected signals are averaged to provide an increased dynamic range. Because the response characteristics of each transducer $XD_N$ can be improved by exciting it a number of successive times while maintaining an apparent real-time image of the display screen 26, the inherent poor sensitivity of the piezoelectric polymer chosen for the transducer material is overcome.

To accomplish the multiple excitations of a transducer element $XD_N$, a plurality of differential pulsed excitation signals are transmitted on the T+ and T− transmission lines of cable 28 while keeping active the same transducer channel 60 (i.e., without sequencing shift register 84). In between each excitation signal, sufficient time is allowed for detecting reflected ultrasonic signals and delivering them to the ANA OUT line. As the reflected ultrasonic signals are detected, they are signal averaged at a dynamic signal averager in order to produce a single collective signal with a considerably higher dynamic range than any of the individually received signals. Applicants prefer to keep a "running" average—that is, a new average is calculated upon the reception at the dynamic signal averager of each new reflection signal; however, an obvious alternative is to collect all the reflection signals and make a single averaging calculation.

After this process of averaging a plurality of reflection signals from one of the transducer channels 60 is completed, a pulse is sent from the signal processor 30 on the CCLK transmission line of cable 28, thereby producing a digital pulse on the CLK line of the chip 54 which is input to the 16-bit shift register 84. This CLK pulse causes the shift register 84 to shift the single logic 1 value to the next output line, thereby deactivating the previous transducer channel 60 and activating the next transducer channel where the foregoing process is repeated.

Once the digitized and averaged signal representing the detected acoustic reflection or echo is collected, it is stored for a brief amount of time in an acoustic frame buffer which is essentially a high-speed memory system. A cross-point switch responsive to a focus map memory and a sequencer uses selective pieces of data from the acoustic frame buffer and combines this data with weighting factors $W_0$–$W_9$ at multiplier elements. The resulting weighted signals are then input to a summer which performs a summation of all the weighted inputs. A single data stream is then output from the summer to a digital rectifier and low pass filter. Depending on its proximity to a pixel when mapped onto a cartesian coordinate system (linked to the video display as explained hereinafter), this single data stream may be used to provide gray scale information for the pixel location on the screen of the video display 26.

Specifically, in order to convert the image information received from the probe assembly 24 from polar format to cartesian format, the reconstructed, rectified and filtered vector data is subjected to a two-pass process. The first pass samples each vector signal to the nearest vertical (Y) coordinate in a cartesian grid, according to the angle of the beam reconstruction as indicated by the placement of the vector signals on vertical grid lines in FIG. 15. The second pass re-samples the resulting signal into the nearest horizontal (X) coordinate in the cartesian grid as indicated by the arrows in FIG. 15. This scan conversion process is accomplished by first passing each vector output from the digital filter through an angle-dependent sample rate converter and storing the results in a Y, $\theta$ buffer. Then the concentric squares generator 128 takes the Y, $\theta$ converted data and fits it to the nearest point in the cartesian pixel matrix of a video system. A video system provides a memory interface between the concentric squares generator and the pixel memory. In a conventional manner, the video system also provides dynamic pixel memory refresh and video timing and sync signals for the video monitor 26. The pixel information is passed through a gamma correction lookup table of well-known design and then to a digital-to-analog converter before it is displayed on the video monitor 26.

Figure 13A:
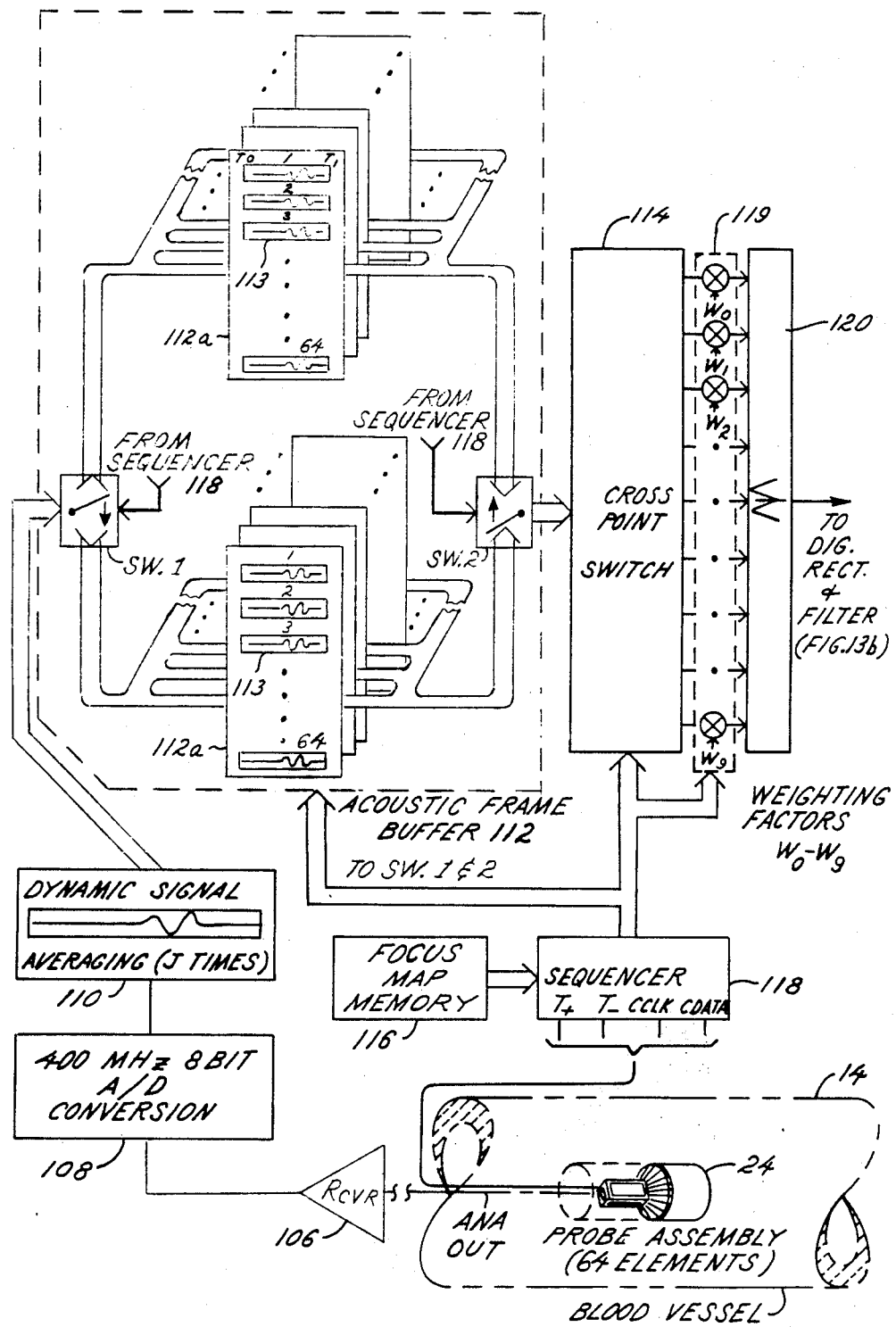
FIGS. 13a and 13b illustrate a schematic block diagram of the in vitro processing and imaging unit of the ultrasonic imaging device according to an exemplary embodiment of the invention.
Figure 13B:
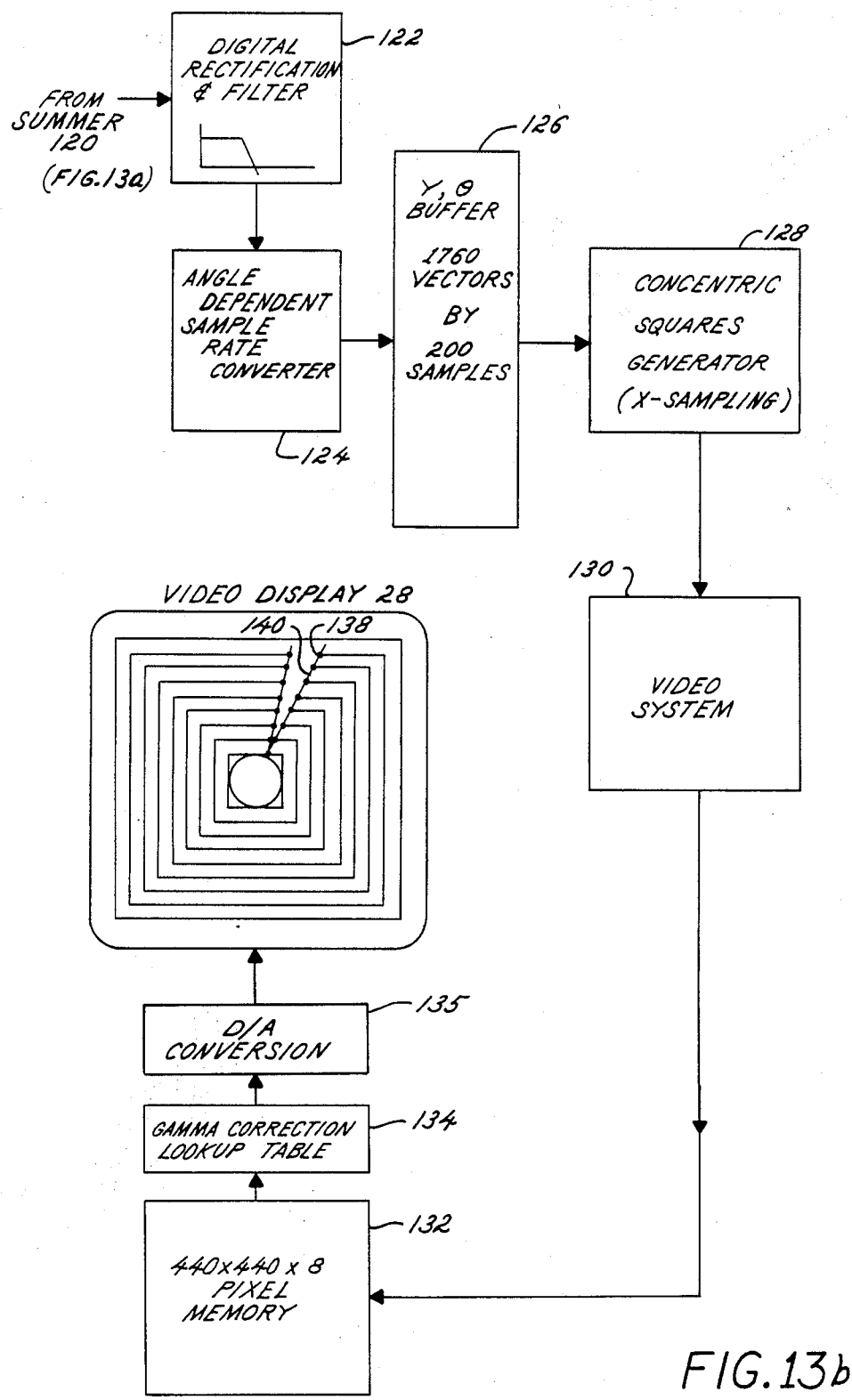

Referring specifically to FIGS. 13a and 13b depicting an image reconstruction system in keeping with the invention, the receiver 106 functions to relay the signals from the probe assembly 24 to the A/D converter 108. The receiver provides full scale voltage amplification of the signals from the probe assembly 24 to the A/D converter 108. Also, the receiver 106 provides impedance matching to the A/D conversion system 108.

From the receiving amplifier 106, the analog-to-digital (A/D) converter 108 takes the signal and converts it into 8-bit two's complement values at a frequency of 400 MHz. Typically, the center frequency of the ultrasonic signals being transmitted and received by the probe assembly 24 is about 20 MHz. The corresponding bandwidth for these signals is about 10 MHz, thereby placing the lower frequency at about 15 MHz and the upper frequency at about 25 MHz. From empirical study, it is found that the sampling rate should be sixteen times the maximum frequency or about 400 MHz. Using this sampling rate for the A/D conversion process allows for image reconstruction which is sufficient to produce very clear images with good resolution.

In keeping with the invention, after the digital values have been produced by the A/D converter 108, they are input to a dynamic signal averager 110 which takes a number of these input 8-bit values and produces a collective 16-bit value. The dynamic signal averager 110 operates to add a number J of the input 8-bit digital values together to produce the resulting 16-bit digital value, and as such the maximum number of 8-bit values which can be added together to produce one 16-bit value without an overflow occurring is 256. Therefore, the maximum acceptable number for J is 256. By adding the incoming 8-bit values together, the dynamic range of the resulting 16-bit value is increased by 3dB each time the total number of summations equals successive powers of two (e.g., 2, 4, 8, 16, etc.) Accordingly, at the maximum number of summations (J equal to 256), the dynamic range is effectively increased by 24dB.

The number of times each of the input signals is summed in the signal averager 110 is predetermined and corresponds exactly to the number of excitation signals sent to each individual transducer element $XD_N$ of the probe assembly 24. For example, in the preferred embodiment 100 individual excitation signals are sent to a particular transducer element $XD_N$ and 100 individual receive signals are generated, each providing information relating to the small cavity. If these excitation signals are sent very close together in time, the corresponding received signals will provide information relating to the cavity during such a short time interval that the information may be considered for the practical purposes of a real-time display as having been simultaneously gathered. The averaging process serves to increase the dynamic range by cancelling any random component of the signals received or generated by the transducer and analog amplification stages of the receiver 106. Therefore, only the stationary parts of the signals are enhanced, thereby producing signals which relate to the particular configuration of the small cavity.

As an important feature in implementing a realtime display, the dynamic signal averager 110 is of a conventional design that provides for the high speed transfer of the collected data to the acoustic frame buffer 112. The dynamic signal averager 110 may be realized using an arithmetic logic unit (ALU) operating in conjunction with a 16-bit memory buffer. In this configuration, the ALU reads one 8-bit word from the A/D converter 108, adds this 8-bit value to the 16-bit buffer value and then stores the resultant value back into the 16-bit buffer. Thus, the ALU operates in a read-modify-write mode wherein the read operation involves reading one 8-bit value from the A/D converter. The modify operation involves adding this 8-bit value to the 16-bit memory buffer value, and the write operation involves writing the resultant value back into the 16bit memory buffer.

The acoustic frame buffer 112 of the present invention is a high-speed memory that stores the digitized waveforms received from the dynamic signal averager 110, and allows these digitized waveforms to be organized such that they may be readily accessed by the cross-point switch 114 during the image reconstruction procedure. In order to allow for the accessing speed which will be required of the acoustic frame buffer 112 by the cross-point switch 114, the buffer includes a plurality of memories 112a, each including a full set of imaging data for the 64 transducer elements. The duplication of the memories 112a accommodates a simultaneous parallel read of a number of data from the 64 digitized waveforms. In an exemplary embodiment of the invention, the acoustic frame buffer 112 is duplicated a total of ten times, thus allowing the cross-point switch 114 to simultaneously read ten different locations of the buffer.

In order to accommodate all of the incoming data which is to be stored while still making available data for reading by the cross-point switch 114, a pair of these duplicated sets of memories 112a is provided as illustrated in FIG. 13a. While one of these sets is being filled with digitized waveform information from the dynamic signal averager 110, the other set of memories, which has already been filled with waveform information, is utilized for reading by the cross-point switch 114 for the image reconstruction. After one of the sets of memories 112a is filled with waveform information and the other set has been read by the cross-point switch 114, the two sets of memories are operatively alternated such that the set of memories which was previously being filled is now read by the cross-point switch while the other set of buffers which was previously being read is now refilled with new waveform information from the dynamic signal averager 110. This process of alternating the two sets of memories 112a is repeated continuously throughout the entire operating period of the system in order to maximize the speed of data flow. For purposes of illustration, the mechanism for alternating between the two sets of memories 112a is shown as synchronized switches SW1 and SW2 in FIG. 13a. The switches SW1 and SW2 are shown to be under the control of a sequencer 118 discussed more fully hereinafter. It will be appreciated by those skilled in the art that the actual implementation of a mechanism for alternating between the two sets of memories 112a is implemented by firmware of conventional design.

As can be seen in FIG. 13a, each memory 112a in the acoustic frame buffer 112 is partitioned into several different sections 113. Each individual section 113 is associated with a particular transducer element $XD_N$, and is used to store the digitized signal information received by the particular transducer element. Each of the individual storage sections 113 is comprised of 2048 16-bit words of high-speed dynamic random access memory (DRAM) and represent a response time of the associated transducer element $XD_N$ from times $t_0$ to $t_1$. Each of these 16-bit words is individually accessible by the cross-point switch 114 during the image reconstruction process. These 16-bit words of the individual storage sections 113 store the various discrete values of the signal received on the associated transducer elements $XD_N$. Accordingly, there are as many individual storage sections 113 as the number of transducer elements $XD_N$ on the probe assembly 24 (e.g., 64).

All of the plurality of memories 112a in one set are written to in a simultaneous manner from the dynamic signal averager 110, and therefore they all contain identical digitized waveform information. Each of the individual memories 112a contain all the signal information necessary to reconstruct a single complete image.

In keeping with the invention, the primary image reconstruction process uses a synthetic-aperture technique of beam-forming which involves delaying, weighting and summing information resulting from band-limited spherical acoustic waves impinging on the transducer elements $XD_N$. Generally, a synthetic-aperture technique is known in Sonar environments. It has also been used to generate real-time images in ultrasonic imaging applications (see, for example, U.S. Pat. Nos. 4,325,257 to Kino et al. and 4,127,034 to Hederman et al.). However, applicants believe they are the first to apply the synthetic-aperture approach to a "closed" array—i.e., a physically non-linear array that is acoustically continuous.

Figure 14:
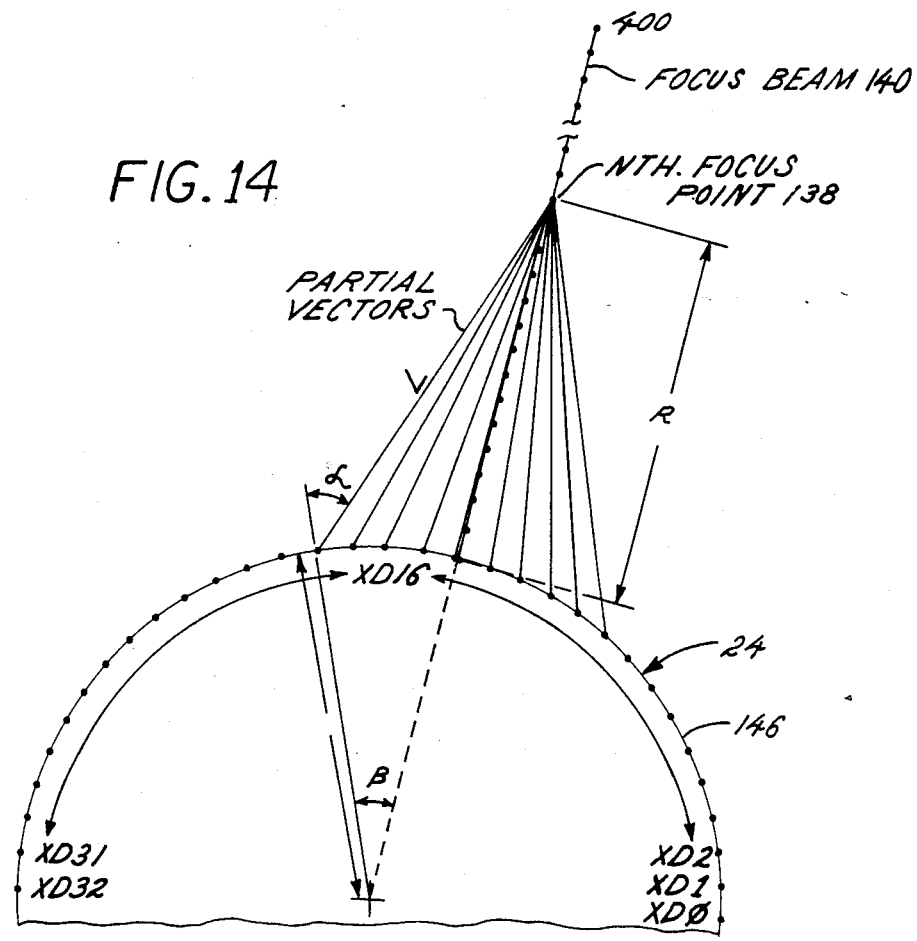
FIG. 14 is a diagrammatic representation of a portion of the array of acoustic transducers and one of a plurality of radial focus beams, each having a plurality of focus points for reconstructing an image derived from partial vectors associated with the ultrasonic signals received by the transducers.

In keeping with the synthetic-aperture approach, the initial image information is generated on a point-by-point basis where the focus points 138 in FIG. 14 are located along a plurality of radial beams or vectors 140 radiating from the geometric center of the array. As suggested by FIG. 15, in the preferred embodiment of the invention, there are 1756 vectors extending from the center of the probe assembly 24 to an outer focus radius 142 that corresponds with the edge of the screen when the data is mapped to the video display 136. Each vector or focus beam 140 is positioned such that it intersects a point on a square 144 (corresponding to the edge of the video screen) circumscribed about the outer focus radius 142 which has 440 points on a side. There are 400 focus points 138 on each vector, and they are evenly spaced along the vector from the surface of the probe assembly 24 to the outer focus radius 142.

Referring more specifically to FIG. 14, there is shown the array of cylindrical transducers $XD_N$ along with one of the 1756 beams or vectors 140. The 400 focus points 138 are evenly spaced on the vector 140, starting from the surface 146 of the probe assembly 24 and extending to the outer focus radius 142. During the reconstruction process, the ultrasonic signals received from a plurality of individual transducer elements $XD_N$ are used to reconstruct the focus points 138 along the selected beam vector 140. In the preferred embodiment of the invention, it has been determined that ten of the 64 transducer elements $XD_N$ effectively contribute reconstruction information for the focus points 138 along the selected beam 140 (hence the ten memories 112a in each pair in FIG. 13a). The first step in reconstructing a beam 140 is the determination of these ten transducer elements $XD_N$, which is done by selecting the ten transducer elements $XD_N$ which are closest to the selected beam.

Since the position relationship between the transducer elements $XD_N$ and the beams is predetermined and remains constant, the information necessary to determine the value of each of the focus points 138 is advantageously pre-calculated in order to prevent the time-consuming steps required to calculate this information. This beam reconstruction focus point information is stored in the focus map 116 which is a high-speed memory and is utilized by the cross-point switch 114 and the weighting elements 119 to properly combine the signals stored in the acoustic frame 112 buffer and to calculate the values of each of the beam focus points 138.

The steps involved in pre-calculating the values stored in the focus map 116 will now be described in greater detail with reference to FIG. 14. For each of the transducer elements $XD_N$ associated with a beam 140, an element angle $\beta$ defines the angle between the selected beam 140 and the transducer element as measured from the center of the probe assembly 24. An angle $\alpha$ is defined by the line normal to the surface of the transducer $XD_N$ being considered and a line L from the transducer element to the focus point 138. Using well-known trigonometric properties, the distance L between the selected transducer element $XD_N$ and the point of focus 138 on the beam 140 is calculated. These distances L are calculated for each of the focus points 138 along the beam 140. The calculated distances L are used to compute delays, which are used to determine which of the 16-bit words in the storage section 112a corresponding to the transducer $XD_N$ under consideration should be selected for weighting in the multipliers 119 and combining in the summer 120. For each focus point 138, the delay values are converted to memory addresses for the appropriate 16-bit words and the addresses are stored into the focus map memory 116. Therefore, in reference to the FIG. 14 which utilizes the information from ten selected transducer elements $XD_N$ to reconstruct each beam, there are calculated ten separate delay values (i.e., addresses) for each focus point 138—one for each of the selected transducer elements used to reconstruct the particular beam under consideration.

As is well known in the art, in order to optimize the image formed by any imaging system with a finite aperture, it is necessary to apodize the aperture. Apodizing the aperture is simply controlling the distribution of system sensitivity across the aperture. In the particular reconstruction approach used herein, a synthetic aperture is constructed with the length of the aperture determined by the number of elements which are summed together for a particular focus point. In the illustrated embodiment, ten elements have been chosen. However, it will be appreciated by those skilled in the art of ultrasonic imaging that the particular number of elements chosen is dependent on the beam profile of each transducer element $XD_N$ as illustrated in FIG. 17 and the depth of the focus points 138.

Figure 17:
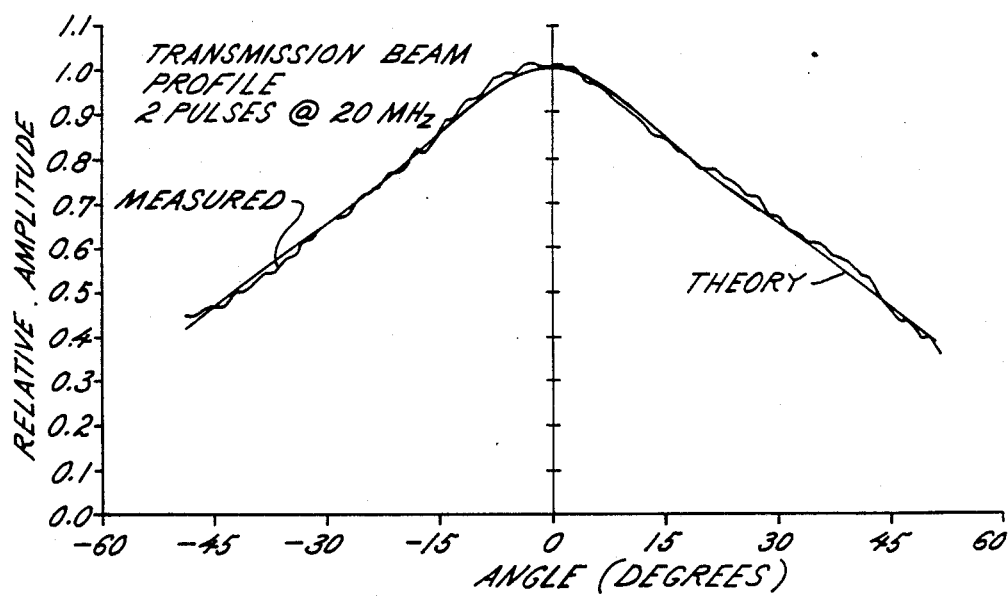
FIG. 17 is a graph in Cartesian coordinates of an exemplary beam profile for each element in the transducer array, where the normalized amplitude as plotted on the ordinate is measured at a constant radius and the beam angle plotted on the abscissa is measured from the center of the cylinder formed by the array.
Figure 18:
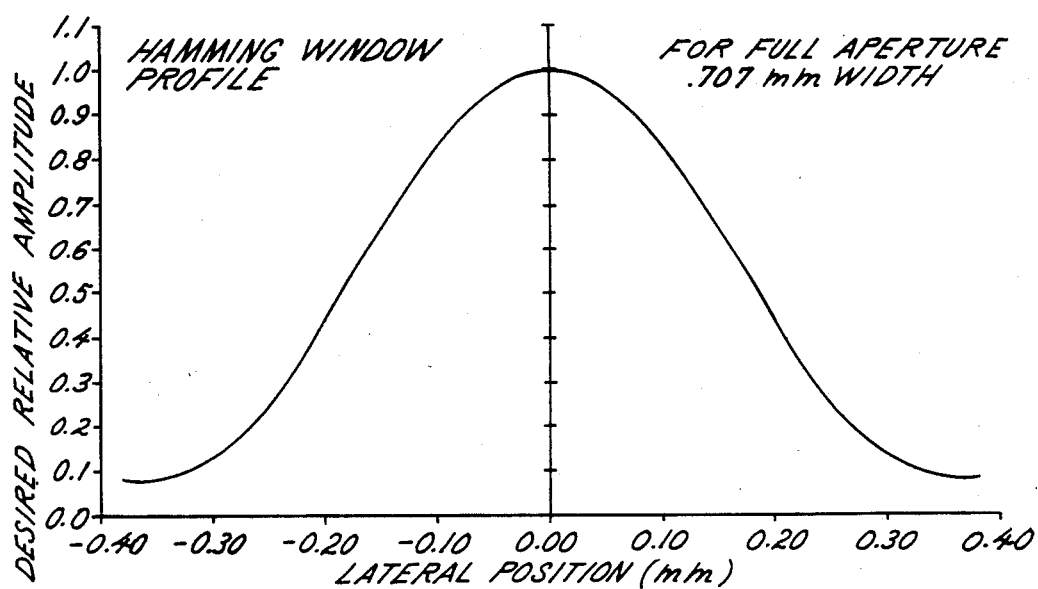
FIG. 18 is a graph in Cartesian coordinates of the Hamming window profile for a single element in the transducer array, where the normalized amplitude is plotted on the ordinate and a circumferential distance from a central radial beam is plotted on the abscissa.

The apodization value is computed as follows: First, a particular focus point 138 is selected and the number of elements to form the synthetic aperture is selected (ten in the illustrated embodiment). Second, a standard Hamming window for the synthetic aperture as illustrated in FIG. 18 is referenced. In the illustrated embodiment, the width of the ten transducer elements is approximately 0.7mm (see FIG. 18). Third, for each transducer element, the position within the Hamming window of FIG. 18 is determined. The normalized amplitude value is the desired apodization value. Fourth, the sensitivity of the element to the focus point is determined by the angle $\alpha$ from the surface of the transducer to the focus point 138. For example, if the value of the angle $\alpha$ in FIG. 14 is a $+15°$, the transmission beam profile in FIG. 17 indicates that the normalized response amplitude is approximately 0.85. This beam profile corresponds to a natural apodization for the aperture. Fifth, in order to apodize the aperture in the desired manner, the raw weight assigned to each delay value is computed from the relationship:

$$\text{raw weight}(i) = \frac{\text{desired amplitude for signal from transducer}(i) \text{ from the Hamming window profile of FIG. 18}}{\text{natural amplitude of signal from transducer}(i) \text{ from the transmission beam profile of FIG. 17}} \quad (5)$$

where i is 0 through 9 for the ten elements used for each focal point.

Sixth, to provide for uniform intensity across the image plane, it is necessary to normalize the weights. This is done because the image plane contains areas which result from summations of various numbers of elements (in this example 10, but the number of elements ranges from 1 to 10). This is done by first summing all raw weights W0 to W9. The final weight is computed by dividing each raw weight by the sum of all raw weights for the particular point:

$$W(i) = \frac{\text{raw weight}(i)}{\sum_{j=1}^{n} \text{raw weight}(j)} \quad (6)$$

where n is the total number of elements summed for this particular focus point.

Figure 15:
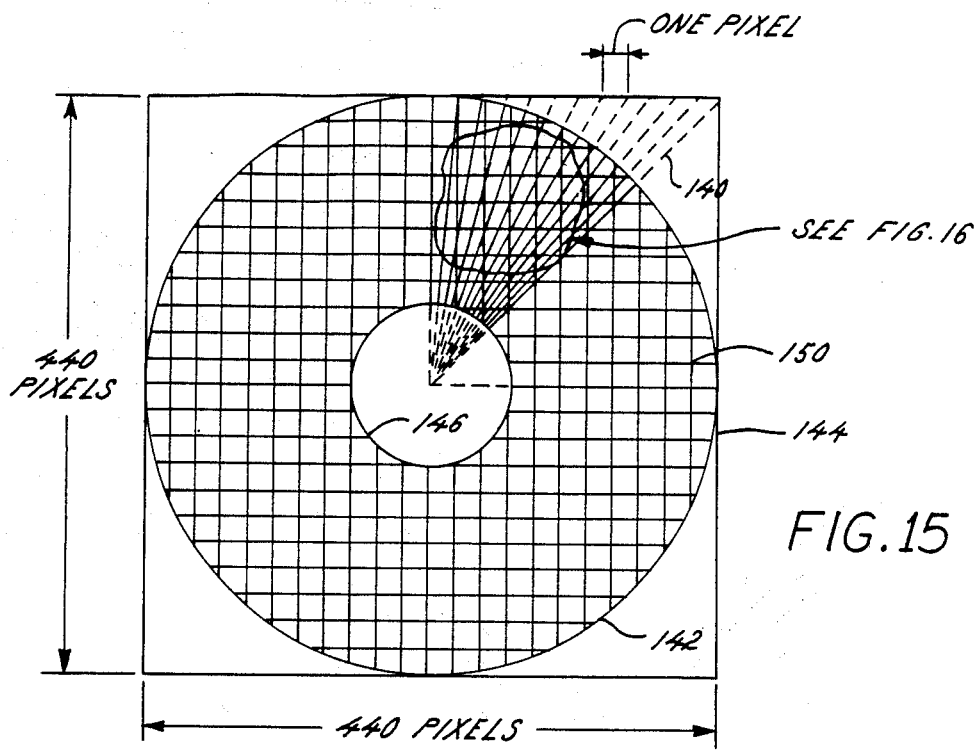
FIG. 15 is a schematic illustration of the screen of a video display used to generate the images shown in FIGS. 2 and 4, showing how the plurality of radial focus beams are mapped onto the pixels of the screen.

By taking into consideration the symmetry which exists for each octant around the focus area as illustrated in FIG. 15, the focus map information only needs to be computed for one octant of the focus area. The focus map information for the remaining octants may be determined from the information computed in the initial octant through very simple manipulations of the data that need not be detailed herein. After the focus map information has been computed, it is stored in the focus map memory 116. This focus map information is utilized by the sequencer 118 to operate the cross-point switch 114 so as to select the proper 16-bit words from the appropriate ten transducer signals stored in the acoustic frame buffer 112 for application of the proper weighting factors $W_N$ at the multipliers 119.

Turning to a more detailed discussion of the acoustic frame buffer 112, the conventional video RAMs or VRAMs (not shown) of the buffer have the desirable feature of operating like high-speed serial shift registers which can be configured to deliver a 16-bit word by simply having 16 VRAMs. An additional one-bit VRAM (not shown) is used to contain time sampling or clocking information and is designed to run synchronously with the output of the acoustic frame buffer 112 for each of the ten transducer elements involved in a beam reconstruction. This sampling information is the time delay portion of the focus map memory 116 and eliminates the need to store actual memory addresses. Thus the re-sequencing of the signal data of the ten transducer elements with a timing signal is equivalent to providing a sequence of addresses which identify the proper 16-bit words in the memory sections 113 during reconstruction of a beam or vector 140.

As for the weighting factors $W_0$-$W_9$, they are also preferably implemented by VRAMs (not shown). There is one weighting factor $W_n$ for each transducer element $XD_N$, each reconstruction vector, and each point on the reconstruction vector. Each weighting factor $W_n$ corresponds to one timing bit in the one-bit VRAM. Therefore, an 8-bit parallel VRAM arrangement, containing apodization values, is clocked by the timing information from the one-bit VRAM to provide to the multiplier 119 a sequence of corresponding weights $W_n$ at the appropriate times. Since the timing information is artificially "recreating" the time-delay part of the focus, the parallel operation of each of the ten transducer channels from the cross-point switch 114 used to reconstruct a focus point 138 is not synchronous. The final output to the summer circuit 120 must be synchronous, however, and therefore each parallel channel from the cross-point switch 114 is first passed through a FIFO (not shown) to realign the data.

In order to control the sequence of beam reconstruction and to deliver excitation and control signals to the probe assembly, the sequencer 118 is preferably a multi-PAL based hardware sequencer. It also optimizes the symmetrical aspects of the reconstruction according to the pre-computed focus map parameters. The sequencer 118 starts with the focus beam 140 at angle zero and sweeps around the 360 degree circle in 1756 steps as implied in FIG. 15. For each vector or beam point 140, the sequencer 118 loads the appropriate VRAM shift registers for each of the nine element channels in focus range. The shift registers are then allowed to clock and data is re-sequenced according to the pre-computed focus parameters of the focus map memory 116. When the sequence is finished the sequencer 118 steps to the next focus beam and the process is repeated until all beams are done.

After the weighting is applied to the ten 16-bit signals at multiplier 119, the signals are combined through the summer 120 to produce a single collective signal. Each of the collective signals produced by the summer 120 corresponds to a value of one of the focus points 138 along the various focus beams 140. The values are produced sequentially with respect to the points 138 on the beams 140, such that a filtering process may be applied to the points along the beam.

In order to accomplish this filtering process, the information from the summer 120 is rectified and filtered in the digital rectification and filter 122 in FIG. 13b. The digital filter 122 is based upon FIR filter coefficient computations found in standard digital filter literature. In an exemplary embodiment of the invention, the filter is a four-point FIR filter with symmetrical coefficients of [0.21,0.5,0.5,0.21] which has been found to be effective in producing the desired low-pass filter characteristics. Through this process, the signal envelope of each of the beams 140, is determined such that the output of the filter 122 is a unipolar baseband signal representing the tissue information received by the reflections or echoes which were used to form the individual beams.

After the filtering process is completed in the digital filter 122, the focus beams 140 comprising a plurality of focus points 138 have been formed through delays and weighting (in the cross-point switch 114 and multipliers 119), and have additionally been rectified and low-pass filtered (in filter 122) to result in beams containing discrete values which represent tissue information gathered from the received ultrasonic signals. It should be noted that because of the small size of the imaging area, the attenuation of the reflected ultrasonic waves caused by the distance of travel through a medium is negligible. Therefore, there is no compensation for this type of attenuation in the preferred image reconstruction technique. However, distance attenuation may be dealt with in a digital manner in the focus map memory 116 if desired.

Figure 16:
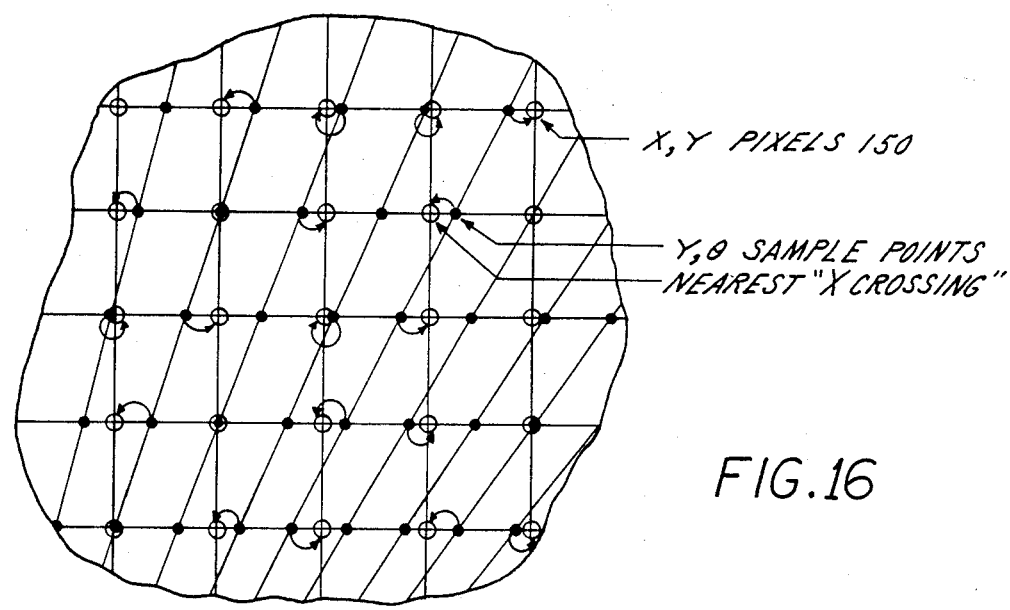
FIG. 16 is an enlarged and partial view of the schematic in FIG. 15, illustrating how the points comprising the focus beams are matched with the pixels of the video display screen.

After the radial focus beams 140 have been formed, they are mapped to a cartesian grid so the information may be presented on a standard video display 26. The X, Y pixel points 150 in FIGS. 15 and 16 comprising the cartesian grid must be filled with data from the focus points 138 on the beams 140. In order to fill the grid with focus points 138, the angle-dependent sample rate converter 124 first maps each of the focus points 138 either up or down so as to place them on the nearest vertical grid crossings as shown in FIG. 16. At this point, the vector data which is now referenced by a "Y" cartesian coordinate and an angle $\theta$, is converted to an 8-bit value since this is much more practical for modern display devices. This allows the various points to take on 256 different "gray" values for display, which is more than adequate for normal visual perception of the images. The resultant points then are stored in the Y, $\theta$ memory buffer 126.

An X-sampling process is then carried out by the concentric squares generator 128 which performs an "X"-sampling process whereby each cartesian pixel point 150 is filled with information from the nearest point in the Y, $\theta$ buffer as shown in FIG. 16. After this is completed, each cartesian pixel point 150 will contain an 8-bit value representative of the value of the nearest focus point 138 produced by the beam reconstruction. In a conventional manner, the pixel information is placed in the proper area of the pixel memory system 132 by the video system 130, and the information is then passed through a gamma correction lookup table 134 of known construction and a digital-to-analog converter 135 before it is displayed on the video monitor 26.

From the foregoing description of the preferred embodiment of the invention, it will be appreciated that a new ultrasonic imaging device is provided for imaging inside cavities whose small sizes have heretofore made such imaging impossible. In the first instance, the invention is intended to find most usefulness in medical diagnostic and therapeutic techniques. However, applicants envision a broad range of applications for the imaging device, including any solution to a problem that may be aided by imaging inside a very small cavity. In this regard, the precise nature of the imaging plane P (FIG. 5) may be subject to the problems addressed and any suggested solutions. For example, the axes of the transducer elements may be angled with respect to the longitudinal axis of the probe in order to provide forward viewing in the cavity. Such forward viewing may be necessary if a laser device is used in connection with the invention. Forward viewing would allow the laser device to be guided using the visual aid of a real-time image of the target area as provided by the invention. It is anticipated that in such forward viewing applications, the apparatus and method of accumulating the imaging data and its processing remain essentially the same.

What is claimed is:

1. An imaging device for emitting ultrasonic acoustic waves and providing a useable image in response to detection of reflections of said ultrasonic acoustic waves, said imaging device comprising:
   a body for insertion into a cavity;
   an array of transducer elements mounted to said body for generating first electrical signals containing imaging information in response to said reflections of said ultrasonic acoustic waves;
   a cable connecting said body to an environment external of said cavity and including at least one signal channel for transporting said first electrical signals;

means mounted on said body and proximate to said array of transducer elements for receiving said first electrical signals from said array of transducer elements and converting said first electrical signals to second electrical signals that may be transmitted along said at least one channel in said cable without significant loss of imaging information;

a processor responsive to said second electrical signals from said cable for providing imaging data; and a display responsive to said imaging data for providing a visual image of said cavity and its surrounding structure.

2. An imaging device as set forth in claim 1 wherein said processor provides excitation signals to said array of transducer elements via at least one channel in said cable; and said means being responsive to said processor for directing each of said excitation signals to an appropriate at least one of the transducer elements in said array of transducer elements.

3. An imaging device as set forth in claim 2 wherein said means includes means for providing low impedance paths through transducer elements in said array of transducer elements adjacent said at least one of the transducer elements that receives one of said excitation signals.

4. An imaging device as set forth in claim 2 wherein said processor incorporates further means for applying a plurality of successive excitation signals to said at least one of the transducer elements in said array of transducer elements; and said processor including means (1) for averaging to one signal the plurality of successive second signals resulting from the acoustic reflections generated by said plurality of successive excitation signals.

5. An imaging device as set forth in claim 4 wherein said processor includes means (2) for accumulating and processing all of the averaged signals from said array of transducer elements with sufficient speed so as to maintain an apparent realtime image on said display.

6. An imaging device as set forth in claim 1 wherein said body is fitted to one end of a conventional catheter and includes means for accommodating conventional uses of said catheter.

7. An imaging device as set forth in claim 6 wherein said accommodating means includes a central bore through said body that is in direct communication with a guide wire lumen in said conventional catheter.

8. An imaging device as set forth in claim 1 wherein said means are transimpedance amplifiers and said first electrical signals are low current signals from said array of transducer elements where said array of transducer elements are composed of material that act as a high impedance source of said low current signals, said transimpedance amplifiers converting said low current signals to said second signals which are high voltage signals for transmission through said at least one channel in said cable to said processor.

9. A device as set forth in claim 1 wherein said array of transducer elements comprises a continuous piezoelectric material fitted over a plurality of conductive strips mounted on said body for receiving said first electrical signals from said piezoelectric material such that each conductive strip cooperates with an area of said continuous piezoelectric material overlying said strip to define one of said transducer elements in said array.

10. A device as set forth in claim 9 wherein said continuous piezoelectric material has a form of a ring and has an outside diameter of approximately four millimeters or less.

11. A device as set forth in claim 9 wherein the piezoelectric material of said array of transducer elements is a polymer selected from the group of PVDF, P(VDF-TrFE), P(VDF-TFE), a composite material consisting of a polymer and a ceramic such as PZT, or a depositable material such as ZnO.

12. A method of imaging characteristics of a small cavity and surrounding structure using a probe assembly provided with an array of transducer elements and located at the end of a transmission line, said method comprising the steps of:

inserting said probe assembly into small cavity, emitting ultrasonic signals into said small cavity and surrounding structure by selectively exciting at least one of said transducer elements, detecting reflections of said ultrasonic signals by receiving first electrical signals generated by said reflections impinging on at least one of said transducer elements, converting said first electrical signals to second electrical signals suitable for transmission on said transmission line, transmitting said second electrical signals on said transmission line to an area external from said small cavity, processing said second electrical signals into image data, and displaying said image data on a visual display.

13. A method as set forth in claim 12 wherein the elements in said array of transducer elements are excited in a predetermined sequence and repeating said predetermined sequence at a cycle frequency allowing the displaying of said image data to simulate a real-time performance.

14. A method as set forth in claim 12 wherein at least one element is excited at each step in said predetermined sequence and each step is repeated a plurality of times in one cycle of said predetermined sequence, said method including the additional step of, averaging a plurality of said second electrical signals resulting from the repetition of each step in said predetermined sequence and thereby providing an averaged electrical signal with a higher dynamic range than any one of said second electrical signals.

15. In a system for approximating real-time images of a structure including a probe assembly having an array of transducer elements for collecting image information and a remotely located high-speed memory for storing said image information, a method comprising the steps of:

a. exciting at least one of said array of transducer elements into mechanical vibration a plurality of times so as to generate ultrasonic waves for propagating through said structure;

b. detecting and averaging electrical signals derived from the excitation of at least one of said array of transducer elements in response to the reflections of said ultrasonic waves impinging on said array of transducer elements;

c. storing said average of said detected signals in said high-speed memory;

d. incrementing to a next at least one of said array of transducer elements in accordance with a predetermined sequence and repeating steps (a) through (c);

e. repeating steps (a) through (d) until end of said sequence;

f. finding values from the averages stored in said high-speed memory for a plurality of focal points spatially distributed about said probe assembly; and g. mapping onto a display screen said focal points such that said values for all the focus points required for each frame of said display screen may be determined at a sufficiently high rate of speed so as to maintain the visual appearance of a real-time image.

16. The method of claim 15 wherein said array of transducer elements is in part composed of an acoustically continuous piezoelectric material of high electrical impedance characteristics, said method including the step of:

h. providing low impedance paths that effectively shunt the high impedance characteristics of those transducer elements adjacent said at least one transducer elements in steps (a) and (b) during the time said at least one transducer elements is active so as to provide the best beam pattern for determining the focal points of step (f).

17. The method of claim 15 wherein said structure includes a small cavity having approximately the size of a human coronary artery and said method includes the step of:

i. inserting said probe assembly into said small cavity.

18. The method of claim 15 wherein the step of detecting and averaging signals derived from the excitation of at least one of said array of transducer elements in response to the reflections of said ultrasonic waves impinging on said array of transducer elements includes the steps of:

j. detecting reflections of said ultrasonic signals by receiving first electrical signals generated by said at least one transducer element in response to said reflections impinging thereon;

k. converting said first electrical signals to second electrical signals suitable for transmission on a transmission line connecting said probe assembly to said remotely located high-speed memory; and l. transmitting said second electrical signals on said transmission line to said remotely located high-speed memory.

19. The method of claim 18 wherein the averaging of the signals derived from said array of transducer elements occurs as the signals are generated so as to maintain a running average.

20. The method of claim 18 wherein said first electrical signals are low current signals and the material comprising said transducer elements serves as a high impedance source of said first electrical signals and said second electrical signals are high voltage signals suitable for transmission over said transmission line without significant loss of image information contained in said second electrical signals.

21. A system for providing images of the interior of a small cavity and surrounding structure comprising:

a probe assembly having an array of transducer elements for generating (1) ultrasonic waves in response to excitation signals and (2) imaging signals in response to reflections of said ultrasonic waves impinging on said array;

means (1) remote from said probe assembly for generating said excitation signals and control signals;

sequencing means (2) on-board said probe assembly responsive to said control signals for selectively and sequentially distributing said excitation signals to said array of transducer elements and providing a plurality of said excitation signals in succession to a same at least one transducer element in said array of transducer elements;

means (3) responsive to the imaging signals derived from the reflections of said plurality of successive excitation signals impinging on said array of transducer elements for averaging said imaging signals and providing an averaged imaging signal;

a processor responsive to said averaged imaging signal for providing display data; and a display responsive to said display data for providing a visual image.

22. A system as set forth in claim 21 wherein said array of transducer elements comprises an acoustically continuous piezoelectric material, said system including:

means (4) for providing low impedance paths that effectively shunts those transducer elements that are at least adjacent to said at least one transducer element that receives said excitation signal.

23. A system as set forth in claim 21 wherein said processor includes means (5) for providing new display data to said display at sufficient speed so that the image provided by said display simulates a real-time image.

24. A system as set forth in claim 21 including:

means (6) on-board said probe assembly for receiving said imaging signals directly from said array of transducer elements and converting said imaging signals from a first form to a second form such that the converted imaging signals may travel over a transmission line in a cable without substantial loss of imaging information.

25. A system as set forth in claim 21 wherein said excitation signals are delivered to said array of transducer elements via a cable having a number of transmission channels that is less than the number of steps in a predetermined sequence of excitation of said elements that provides a full set of image data for said display, and wherein said means (7) on-board said probe assembly distributes said excitation signals from said cable to said array of transducer elements in order to excite selected ones of said array of transducer elements in said predetermined sequence.

26. A system as set forth in claim 21 wherein said array of transducer elements comprises an acoustically continuous piezoelectric material fitted over a plurality of conductive strips mounted to a body portion of said probe assembly for delivering said excitation signals to said material and receiving said imaging signals from said material such that each conductive strip cooperates with an area of said material overlying said strip to define one of said transducer elements in said array.

27. In an ultrasonic imaging system, a probe assembly responsive to a source of excitation signals for insertion into a small cavity, said probe assembly comprising, in combination:

a body;

a transducer material forming an acoustically continuous surface and mounted to said body for generating ultrasonic acoustic waves in response to said excitation signals from said source and for generating imaging signals in response to the impinging of reflections of said ultrasonic acoustic waves;

a plurality of conductive traces on said body and underlying said transducer material;

a ground plane overlying said transducer material;

a plurality of elements forming an array, each of said elements comprising a conductive trace, a portion of said transducer material overlying said conductive trace and said ground plane such that application of said excitation signal from said source to at least one of said conductive traces causes an area of said transducer material proximate to or overlying said conductive trace to mechanically vibrate and generate said ultrasonic acoustic waves and reflections of said ultrasonic imaging devices impinging on said transducer material causes the generation of said imaging signals on at least one of said conductive traces; and means (1) on-board said body for processing said excitation signals prior to their delivery to at least one of said conductive traces and processing said imaging signals prior to their delivery to a remote imaging device.

28. A probe assembly as set forth in claim 27 including:

means (2) on-board said body for providing a broad beam pattern by effectively shunting at least those elements immediately adjacent the element or elements including said at least one of said conductive traces receiving an excitation signal from said source.

29. A probe assembly as set forth in claim 28 wherein said means (2) also effectively shunts at least those elements immediately adjacent the element or elements generating an imaging signal in response to the impinging of reflections of said ultrasonic acoustic waves.

30. A probe assembly as set forth in claim 27 wherein the body is comprised of material having high acoustic impedance and said probe has a shape such that the resonant effects which occur due to energy reverberating through said body in response to the mechanical vibration of an element do not interfere with the acoustic behavior of said transducer material in the range of frequencies used to generate an ultrasonic image.

31. A probe assembly as set forth in claim 30 wherein said body is composed of material having high acoustic impedance and said transducer material is mounted on a hollow cylindrical portion of said body where the wall of said cylindrical portion has a thickness d that is equal to or less than V/2f, where f is the nominal frequency of the acoustic waves generated by said plurality of elements and V is the velocity of said acoustic waves through the material comprising said body.

32. A probe assembly as set forth in claim 27 wherein said ultrasonic imaging system provides said probe assembly with said excitation pulses in a serial format and said means (1) includes means (3) for distributing said excitation pulses to said plurality of elements in a predetermined sequence.

33. A probe assembly as set forth in claim 27 wherein said means (1) includes means (4) for converting said imaging signals to a format suitable for transmission over a cable without significant loss of imaging information.

34. A probe assembly as set forth in claim 33 wherein said transducer material has a high electrical impedance, said cable has a low electrical impedance and said means (4) is a transimpedance device in the range of frequencies used to generate an ultrasonic image.

35. A probe assembly as set forth in claim 27 wherein said body includes means (5) for attaching said probe assembly to an end of a conventional catheter such that whatever procedure and devices normally used with said conventional catheter are unaffected by the presence of said probe assembly.

36. An imaging device for emitting ultrasonic acoustic waves and providing a useable image in response to detection of reflections of said ultrasonic acoustic waves, said imaging device comprising:

a body for insertion into a small cavity;

an array of transducer elements mounted to said body for generating first electrical signals in response to said reflections of said ultrasonic acoustic waves and emitting said ultrasonic acoustic waves in response to second electrical signals;

a cable connecting said body to an environment external of said cavity and having a number of signal channels for transporting said first and second electrical signals where said number of signal channels is less than the number of elements in said array;

a signal processor for receiving said first electrical signals from said cable and transmitting to said cable said second electrical signals; and distribution means mounted on said body for serially receiving said second electrical signals from said cable and applying said second electrical signals to said array of transducer elements in a predetermined sequence of selected elements, where the number of steps in the sequence is greater than the number of signal channels in said cable.

37. An imaging device as set forth in claim 36 where said array of transducer elements comprises a plurality of conductive traces underlying a continuous piezoelectric material, said distribution means delivering each of said second electrical signals to at least one of said conductive traces, thereby causing an area of said continuous piezoelectric material overlying said conductive trace to vibrate at ultrasonic frequencies.

38. An imaging device as set forth in claim 37 where said continuous piezoelectric material is characterized by a high electrical impedance and said imaging device includes means mounted to said body for effectively shunting at least those elements immediately adjacent the element or elements receiving one of said second signals from said signal processor.

* * * * *